(12) United States Patent
Uhrich et al.

(10) Patent No.: US 10,138,203 B2
(45) Date of Patent: Nov. 27, 2018

(54) ANTIBACTERIAL AGENTS

(71) Applicant: Rutgers, the State University of New Jersey, New Brunswick, NJ (US)

(72) Inventors: Kathryn E. Uhrich, New Brunswick, NJ (US); Allison Faig, Madison, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 15/318,610

(22) PCT Filed: Jun. 15, 2015

(86) PCT No.: PCT/US2015/035854
 § 371 (c)(1),
 (2) Date: Oct. 19, 2017

(87) PCT Pub. No.: WO2015/195563
 PCT Pub. Date: Dec. 23, 2015

(65) Prior Publication Data
 US 2017/0217878 A1    Aug. 3, 2017

Related U.S. Application Data

(60) Provisional application No. 62/012,850, filed on Jun. 16, 2014.

(51) Int. Cl.
  *C07C 233/47*   (2006.01)
  *A61K 9/127*    (2006.01)
  *A61K 45/06*    (2006.01)
  *A61K 31/23*    (2006.01)
  *C07C 235/06*   (2006.01)
  *A61K 8/42*     (2006.01)
  *A61Q 17/00*    (2006.01)
  *A61Q 19/10*    (2006.01)
  *C09D 5/14*     (2006.01)

(52) U.S. Cl.
  CPC ............ *C07C 233/47* (2013.01); *A61K 8/42* (2013.01); *A61K 9/1272* (2013.01); *A61K 31/23* (2013.01); *A61K 45/06* (2013.01); *A61Q 17/005* (2013.01); *A61Q 19/10* (2013.01); *C07C 235/06* (2013.01); *C09D 5/14* (2013.01); *Y02A 50/401* (2018.01); *Y02A 50/473* (2018.01); *Y02A 50/475* (2018.01); *Y02A 50/478* (2018.01); *Y02A 50/481* (2018.01)

(58) Field of Classification Search
  CPC .... C07C 233/47; C07C 233/48; C07C 233/49
  See application file for complete search history.

(56) References Cited

U.S. PATENT DOCUMENTS

| 4,065,598 | A  | 12/1977 | Takahashi et al. |
| 4,559,157 | A  | 12/1985 | Smith et al. |
| 4,608,392 | A  | 8/1986  | Jacquet et al. |
| 4,820,508 | A  | 4/1989  | Wortzman |
| 4,938,949 | A  | 7/1990  | Borch et al. |
| 4,992,478 | A  | 2/1991  | Geria |
| 6,328,988 | B1 | 12/2001 | Uhrich et al. |
| 6,365,146 | B1 | 4/2002  | Uhrich et al. |
| 6,497,895 | B2 | 12/2002 | Uhrich et al. |
| 7,262,221 | B2 | 8/2007  | Uhrich et al. |
| 7,470,802 | B2 | 12/2008 | Uhrich et al. |

(Continued)

FOREIGN PATENT DOCUMENTS

| JP | 04326209       | 12/1992 |
| WO | 2000065024 A2  | 11/2000 |

(Continued)

OTHER PUBLICATIONS

Karlsson (Journal of Colloid and Interface Science, 252, 290-296, 2002).*

(Continued)

*Primary Examiner* — Pancham Bakshi
(74) *Attorney, Agent, or Firm* — Viksnins Harris Padys Malen LLP

(57) ABSTRACT

The invention provides an antibacterial compound of formula (I) or a salt thereof, as well as an antibacterial compound of formula (II) or a salt thereof, wherein R1, R2, X, Y and n have any of the values defined in the specification.

15 Claims, 12 Drawing Sheets

(56) References Cited

U.S. PATENT DOCUMENTS

| | | |
|---|---|---|
| 8,192,754 B2 | 6/2012 | Uhrich et al. |
| 8,846,850 B2 | 9/2014 | Uhrich et al. |
| 9,434,681 B2 | 9/2016 | Uhrich et al. |
| 9,630,905 B2 | 4/2017 | Uhrich et al. |
| 2004/0198641 A1 | 10/2004 | Uhrich et al. |
| 2005/0089504 A1 | 4/2005 | Uhrich et al. |
| 2008/0057026 A1 | 3/2008 | Uhrich et al. |
| 2009/0175932 A1 | 7/2009 | Uhrich et al. |
| 2011/0008396 A1 | 1/2011 | Moghe et al. |
| 2011/0229416 A1 | 9/2011 | Uhrich et al. |
| 2012/0022159 A1 | 1/2012 | Uhrich et al. |
| 2012/0039983 A1 | 2/2012 | Uhrich et al. |
| 2012/0219598 A1 | 8/2012 | Uhrich et al. |
| 2012/0225926 A1 | 9/2012 | Uhrich et al. |
| 2018/0037840 A1 | 2/2018 | Uhrich et al. |

FOREIGN PATENT DOCUMENTS

| | | | |
|---|---|---|---|
| WO | 2001005873 A1 | 1/2001 | |
| WO | 2003005959 A2 | 1/2003 | |
| WO | 2003047518 A2 | 6/2003 | |
| WO | 2003103594 A2 | 12/2003 | |
| WO | 2005074887 A2 | 8/2005 | |
| WO | 2009039505 A1 | 3/2009 | |
| WO | 2013188882 A1 | 12/2013 | |

OTHER PUBLICATIONS

Allen, et al., "Nano-engineering block copolymer aggregates for drug delivery", Colloids and Surfaces B: Biointerfaces 16:3-27 (1999).

Amara, et al., "Covalent Inhibition of Bacterial Quorum Sensing", J Am Chem Soc 131(30), 10610-10619 (2009).

Binder, et al., "Charge-dependent translocation of the Trojan peptide penetratin across lipid membranes", Biophys J 85(2), 982-995 (2003).

Boucher, et al., "Bad bugs, no drugs: no ESKAPE! An update from the Infectious Diseases Society of America", Clin Infect Dis 48(1), 1-12 (2009).

Breukink, et al., "Binding of Nisin Z to bilayer vesicles as determined with isothermal titration calorimetry", Biochemistry 39(33), 10247-10254 (2000).

Brogden, "Antimicrobial peptides: pore formers or metabolic inhibitors in bacteria?", Nature Reviews Microbiology 3, 238-250 (2005).

Buijnsters, et al., "Cationic Gemini Surfactants Based on Tartaric Acid: Synthesis, Aggregation, Monolayer Behaviour, and Interaction with DNA", Eur J Org Chem, 1397-1406 (2002).

Calvez, et al., "Parameters modulating the maximum insertion pressure of proteins and peptides in lipid monolayers", Biochimie 91(5), 718-733 (2009).

Camejo, et al., "The extracellular matrix on atherogenesis and diabetes-associated vascular disease", Atherosclerosis Supplements, vol. 3, pp. 3-9, 2002.

Cammas, et al., "Functional poly[(ethylene oxide)—co-(☐-benzyl-L-aspartate)] polymeric micelles: block copolymer synthesis and micelles formation", Macromol. Chem. Phys., 196, pp. 1899-1905, 1995.

Chemical Abstract of, JP-6305820, 1994.

Chnari, et al., "Engineered polymeric nanoparticles for receptor-targeted blockage of oxidized low density lipoprotein uptake and atherogenesis in macrophages", Biomacromolecules 7(6), 1796-1805 (2006).

Chnari, et al., "Nanoscale anionic macromolecules can inhibit cellular uptake of differentially oxidized LDL", Biomacromolecules 7 (2), 597-603 (2006).

Chnari, et al., "Nanoscale anionic macromolecules for selective retention of low-density lipoproteins", Biomaterials 26(17), 3749-3758 (2005).

Djodjevic, et al., "Polymeric Micelles Based on Amphiphilic Scorpion-like Macromolecules: Novel Carriers for Water-Insoluble Drugs", Pharmaceutical Research, 22(1), pp. 24-32, 2005.

Djordjevic, et al., "Amphiphilic Scorpion-like Macromolecules as Micellar Nanocarriers", Journal of Bioactive and Compatible Polymers, vol. 23 (6), 532-551 (2008).

Djordjevic, et al., "Amphiphilic Star-Like Macromolecules as Novel Carriers for Topical Delivery of Nonsteroidal Anti-Inflammatory Drugs", AAPS PharmSci, 5 (4), pp. 1-12, 2003.

Domingues, et al., "Interaction of the antimicrobial peptide gomesin with model membranes: a calorimetric study", Langmuir 29, 8609-8618 (2013).

Dubertret, et al., "In vivo Imaging of Quantum Dots Encapsulated in Phospholipid Micelles", Science 298, 1759-1762 (2002).

Epand, et al., "Dual mechanism of bacterial lethality for a cationic sequence-random copolymer that mimics host-defense antimicrobial peptides", J Mol Biol 379(1), 38-50 (2008).

Faig, et al., "Biscationic Tartaric Acid-Based Amphiphiles: Charge Location Impacts Antimicrobial Activity", Langmuir 31(43), 11875-1185 (2015).

Faig, et al., "Cationic amphiphiles as disruptive antimicrobial agents", Abstract No. 434, 248th ACS National Meeting & Exposition, San Francisco, California, 1 page, (Jun. 16, 2014).

Faig, et al., "Cationic amphiphiles as disruptive antimicrobial agents", Poster, 248th ACS National Meeting & Exposition, San Francisco, California (Aug. 2014).

Faig, "Design, Synthesis, and Characterization of Bioactive Amphiphiles for Therapeutic Applications", Dissertation Defense Presentation, Rutgers, the State University of New Jersey, 37 pages, (Apr. 2015).

Faig, "Design, Synthesis, and Characterization of Bioactive Amphiphiles for Therapeutic Applications", Dissertation, Rutgers, the State University of New Jersey, 171 pages, (Oct. 2015).

Gabriel, et al., "Interactions between antimicrobial polynorbornenes and phospholipid vesicles monitored by light scattering and microcalorimetry", Langmuir 24(21), 12489-12495 (2008).

Gabriel, et al., "Synthetic mimic of antimicrobial peptide with nonmembrane-disrupting antibacterial properties", Biomacromolecules 9, 2980-2983 (2008).

Gao, et al., "A model of micellization for block copolymers in solutions", Macromolecules, vol. 26, pp. 7353-7360, 1993.

Gitsov, et al., "Micelles with highly branched nanoporous interior: solution properties and binding capabilities of amphiphilic copolymers with linear dendritic architecture", Journal of Polymer Science: Part A: Polymer Chemistry, vol. 38, pp. 2711-2727, 2000.

Grenier, et al., "The antibacterial activity of 4,4'-bipyridinium amphiphiles with conventional, bicephalic and gemini architectures", Bioorganic & Medicinal Chemistry Letters 22(12), 4055-4058 (2012).

Harmon, et al., "In Vitro Evaluation of Amphiphilic Macromolecular Nanocarriers for Systemic Drug Delivery", Journal of Bioactive and Compatible Polymers, 24, pp. 185-197, 2009.

Iverson, et al., "Controllable inhibition of cellular uptake of oxidized low-density lipoprotein: Structure-function relationships for nanoscale amphiphilic polymers", Acta Biomaterialia 6, 3081-3091 (2010).

Karlsson, et al., "Compaction of DNA by Gemini Surfactants: Effects of Surfactant Architecture", Journal of Colloid and Interface Science 252, 290-296 (2002).

Kataoka, et al., "Block copolymer micelles for drug delivery: design, characterization and biological significance", Adv Drug Deliv Rev. 47(1):113-31 (2001).

Kennedy, et al., "Determinants of Calcineurin Binding to Model Membranes", Biochemistry 36(44), 3579-13585 (1997).

Klancnik, et al., "Evaluation of Diffusion and Dilution Methods to Determine the Antibacterial Activity of Plant Extracts", J Microbiol Methods 81(2), 121-126 (2010).

Kleinschmidt, et al., "Structural transitions in short-chain lipid assemblies studied by (31)P-NMR spectroscopy", Biophys J 83(2), 994-1003 (2002).

Kreig, et al., "Micelle formation of randomly grafted copolymers in slightly selective solvents", Journal of Chemical Physics, vol. 115, No. 13, pp. 6243-6251, 2001.

(56) References Cited

OTHER PUBLICATIONS

Ladow, et al., "Bicephalic amphiphile architecture affects antibacterial activity", European Journal of Medicinal Chemistry 46, 4219-4226 (2011).
Langer, et al., "New methods of drug delivery", Science, 249, pp. 1527-1533, 1990.
Laverty, et al., "The potential of antimicrobial peptides as biocides", International Journal of Molecular Sciences 12, 6566-6596 (2011).
Ling, et al., "A new antibiotic kills pathogens without detectable resistance", Nature 517(7535), 455-459 (2015).
Ling, et al., "Erratum: A new antibiotic kills pathogens without detectable resistance", Nature 520(7547), 388 (2015).
Liu, et al., "Nontoxic membrane-active antimicrobial arylamide oligomers", Angewandte Chemie-International Edition 43, 1158-1162 (2004).
Liu, et al., "Unimolecular micelles: Synthesis and characterization of amphiphilic polymer systems", Journal of Polymer Science, Part A:P Polymer Chemistry, 37(6), 703-711 (1999).
Livne, et al., "Design and characterization of a broad-spectrum bactericidal acyl-lysyl oligomer", Chemistry Biology 16, 1250-1258 (2009).
Martin, et al., "Colloidal and biological properties of cationic single-chain and dimeric surfactants", Colloids and Surfaces B: Biointerfaces 114, 247-254 (2014).
Moghimi, et al., "Exploiting bone marrow microvascular structure for drug delivery and future therapies", Advanced Drug Delivery Reviews, vol. 17, pp. 61-73, 1995.
Moghimi, et al., "Long-circulating and target-specific nanoparticles: theory to practice", J. Pharm. Rev. vol. 53(2), pp. 283-318, 2001.
Mondal, et al., "Synthesis and antibacterial properties of carbohydrate-templated lysine surfactants", Carbohydrate Research 346, 588-594 (2011).
Moore, et al., "Room temperature polyesterification", Macromolecules 23 (1), 65-70 (1990).
Orwig, et al., "Comparison of N-terminal modifications on neurotensin(8-13) analogues correlates peptide stability but not binding affinity with in vivo efficacy", J Med Chem 52(7), 1803-1813 (2009).
O'Toole, et al., "Diphosphonium Ionic Liquids as Broad Spectrum Antimicrobial Agents", Cornea 31(7), 810-816 (2012).
Otsuka, et al., "Self-assembly of poly(ethylene glycol)-based block copolymers for biomedical applications", Current Opinion in Colloid & Interface Science 6(1):3-10 (2001).
Palermo, et al., "Cationic Spacer Arm Design Strategy for Control of Antimicrobial Activity and Conformation of Amphiphilic Methacrylate Random Copolymers", Biomacromolecules 13(5), 1632-1641 (2012).
Papisov, et al., "Modeling in vivo transfer of long-circulating polymers (two classes of long circulating polymers and factors affecting their transfer in vivo)", Advanced Drug Delivery Reviews, vol. 16, pp. 127-139, 1995.
Park, et al., "The role of antimicrobial peptides in preventing multidrug-resistant bacterial infections and biofilm formation", International Journal of Molecular Sciences 12, 5971-5992 (2011).
Paslay, et al., "Antimicrobial poly(methacrylamide) derivatives prepared via aqueous RAFT polymerization exhibit biocidal efficiency dependent upon cation structure", Biomacromolecules 13, 2472-2482 (2012).
Patent Cooperation Treaty, International Searching Authority, Search Report and Written Opinion for PCT/US2015/035854, 9 pages, dated Sep. 8, 2015.
Poree, et al., "Nanoscale Amphiphilic Macromolecules with Variable Lipophilicity and Stereochemistry Modulate Inhibition of Oxidized Low-Density Lipoprotein Uptake", Biomacromolecules 14 (8), 2463-2469 (2013).
Rousselle, et al., "New advances in the transport of doxorubicin through the blood-brain barrier by a peptide vector-mediated strategy", Molecular Pharmacology, Vo. 57, pp. 679-686, 2000.
Sahl, "Antimicrobial and host-defense peptides as new anti-infective therapeutic strategies", Nature Biotechnology 24, 1551-1557 (2006).
Schmalenberg, et al., "Cytotoxicity of a unimolecular polymeric micelle and its degradation products", Biomacromolecules 2, pp. 851-855, 2001.
Scorciapino, et al., "A novel dendrimeric peptide with antimicrobial properties: structure-function analysis of SB056", Biophys J 102, 1039-1048 (2012).
Seelig, "Thermodynamics of lipid-peptide interactions", Biochim Biophys Acta 1666(1-2), 40-50 (2004).
Seelig, "Titration calorimetry of lipid-peptide interactions", Biochim Biophys Acta 1331(1), 103-116 (1997).
Sparks, "Design, Synthesis, and Utility of Functionalized Nanoscale Amphiphilic Macromolecules for Biomedical Applications", Dissertation, Rutgers, the State University of New Jersey, 198 pages, (2011).
Sparks, et al., "Synthesis of Functionalized Amphiphilic Scorpion-like Macromolecules for Biomedical Applications", Polymeric Mater: Science & Engineering 97,695 (2007).
Tao, et al., "Novel amphiphilic macromolecules and their in vitro characterization as stabilized micellar drug delivery systems", J. Colloid Interface Sci 298 (1), 102-110 (2006).
Temsamani, et al., "Brain drug delivery technologies: novel approaches for transporting therapeutics", PSTT, vol. 3, No. 5, pp. 155-162, 2000.
Tew, et al., "De Novo Design of Antimicrobial Polymers, Foldamers, and Small Molecules: From Discovery to Practical Applications", Acc Chem Res 43(1), 30-39 (2010).
Tian, et al., "Amphiphilic Scorpion-like Macromolecules: Design, Synthesis and Characterization", Macromolecules 37, 538-543 (2004).
Tian, et al., "Design and synthesis of amphiphilic poly(ethylene glycol) derivaties as a micellar drug delivery system", Polymer Preprints, 43(2), 719-720 (2002).
Tian, et al., "Design and synthesis of amphiphilic poly(ethylene glycol) derivatives as a micellar drug delivery system", Abstracts of Papers, Part 2, 224, (1-2), abstract 748, 224th ACS National Meeting (2002).
Tian, et al., "Novel amphiphilic macromolecules for drug delivery applications: design, synthesis and characterization", in Dissertation, New Brunswick, New Jersey, pp. 13-48, 114-138 and 160-175, 2004.
Torchilin, et al., "Structure and design of polymeric surfactant-based drug delivery systems", J Control Release 73 (2-3):137-72 (2001).
Tounsi, et al., "Thermodynamic and spectroscopic studies of copper (II) complexes with three bis(amide) ligands derived from I-tartaric acid", Journal of Inorganic Biochemistry 99(12), 2423-2435 (2005).
Tuzar, et al., "Micelles of Block and Graft Copolymers in Solutions", Surface and Colloid Science, vol. 15, pp. 1-83, 1993.
Wang, et al., "Comparison of PEG chain length and density on amphiphilic macromolecular nanocarriers: Self-assembled and unimolecular micelles", Acta Biomaterialia, 5, pp. 883-892, 2009.
Wang, et al., "Nanoscale amphiphilic macromolecules as lipoprotein inhibitors: the role of charge and architecture", Int J. Nanomedicine, 2(4), pp. 697-705, 2007.
Williams, et al., "The response-to-retention hypothesis of early atherogenesis", Arteriosclerosis, Thrombosis & Vascular Biology, vol. 15, No. 5, pp. 551-561, 1995.
Wu, et al., "Functionalized Polycarbonate Derived From Tartaric Acid: Enzymatic Ring-Opening Polymerization of a Seven-Membered Cyclic Carbonate", Biomacromolecules 9(10), 2921-2928 (2008).
Zhang, et al., "Cardiolipin Prevents Membrane Translocation and Permeabilization by Daptomycin", Journal of Biological Chemistry 289, 11584-11591 (2014).
Zhang, et al., "Synthesis and antibacterial characterization of gemini surfactant monomers and copolymers", Polymer Chem 3, 907-913 (2012).
Zhao, "Facial amphiphiles in molecular recognition: From unusual aggregates to solvophobically driven foldamers", Current Opinion in Colloid & Interface Science 12(2), 92-97 (2007).

(56) References Cited

OTHER PUBLICATIONS

Zhu, et al., "Super Microcapsules" (SMC. I. Preparation and Characterization of Star Polyethylene Oxide (POE)-Polylactide (PLA) Copolymers, J. Polym. Sci. Polm. Chem., vol. 27, p. 2151, 1989.

* cited by examiner

EXAMPLE PEGylation STRATEGIES

ANTIBACTERIAL AGENTS

CROSS-REFERENCE TO RELATED APPLICATION(S)

This application claims priority from U.S. Provisional Application No. 62/012,850, filed Jun. 16, 2014, which application is herein incorporated by reference.

GOVERNMENT FUNDING

This invention was made with government support under R01 HL107913 awarded by the National Institutes of Health and under P200A120078 awarded by the U.S. Department of Education fellowship for Graduate Assistance in Areas of National Need. The government has certain rights in the invention.

BACKGROUND OF THE INVENTION

The development of antibiotic-resistant bacteria is a prevalent concern that has prompted the development of new antimicrobial agents (Park, et al., *International Journal of Molecular Sciences* 2011, 12, 5971; Laverty, et al., *International Journal of Molecular Sciences* 2011, 12, 6566; Tew, et al., *Accounts of chemical research* 2010, 43, 30; Boucher, et al., *Clinical Infectious Diseases* 2009, 48, 1). As an alternative to conventional antibiotics, antimicrobial peptides (AMPs) have received widespread attention. Many of the naturally occurring AMPs elicit antibacterial activity by targeting the cellular membrane (Park, et al., *International Journal of Molecular Sciences* 2011, 12, 5971; Laverty, et al., *International Journal of Molecular Sciences* 2011, 12, 6566; Tew, et al., *Accounts of chemical research* 2010, 43, 30). Although these peptides have diverse primary structures, many exhibit a net cationic charge and facially amphiphilic secondary structure in which hydrophobic and hydrophilic domains exist on opposite 'faces' of the molecule (Zhao, Y. *Current Opinion in Colloid & Interface Science* 2007, 12, 92); it is the cationic, amphiphilic character that appears to give rise to AMPs' unique mechanism of action (Park, et al., *International Journal of Molecular Sciences* 2011, 12, 5971; Laverty, et al., *International Journal of Molecular Sciences* 2011, 12, 6566; Tew, et al., *Accounts of chemical research* 2010, 43, 30). These AMPs first interact with negatively charged bacterial membranes via electrostatic bonding (Laverty, G.; Gorman, S. P.; Gilmore, B. F. *International Journal of Molecular Sciences* 2011, 12, 6566; Brogden, K. A. *Nature Reviews Microbiology* 2005, 3, 238). After the initial interaction, AMPs' hydrophobic domains interact with the hydrophobic membrane interior, ultimately disrupting the membrane and resulting in cell death (Laverty, G.; Gorman, S. P.; Gilmore, B. F. *International Journal of Molecular Sciences* 2011, 12, 6566; Brogden, K. A. *Nature Reviews Microbiology* 2005, 3, 238). Owing to their membrane-targeting activity, AMPS exhibit reduced instances of bacterial resistance and are promising antibiotic alternatives (Laverty, G.; Gorman, S. P.; Gilmore, B. F. *International Journal of Molecular Sciences* 2011, 12, 6566; Grenier, et al., *Bioorganic & Medicinal Chemistry Letters* 2012, 22, 4055; Ling, et al., *Nature* 2015, advance online publication). However, high production costs and instability in the presence of proteases, has limited their clinical application (Tew, et al., *Accounts of chemical research* 2010, 43, 30; Scorciapino, et al., *Biophys. J.* 2012, 102, 1039; Hancock, R. E. W.; Sahl, H.-G. *Nature Biotechnology* 2006, 24, 1551).

Accordingly, there is a need for new agents that have antibacterial properties.

SUMMARY OF THE INVENTION

Applicant has discovered novel cationic amphiphiles, which may be used as therapeutic compounds. These amphiphiles may also be useful in biomedical applications, including antimicrobial and delivery applications. Research suggests that such cationic amphiphiles can self assemble into micelles, complex with liposomes, or be formulated into nanoparticles for various delivery applications. These amphiphiles could thus be used as therapeutic compounds, as delivery vehicles for bioactives, including oligonucleotides, or for diagnostics. Additionally, these cationic amphiphiles could improve the performance of current antimicrobial products. Thus, therapeutic compounds are described below. In particular, compounds with antibacterial properties are described below.

Accordingly, the invention provides a compound of formula I:

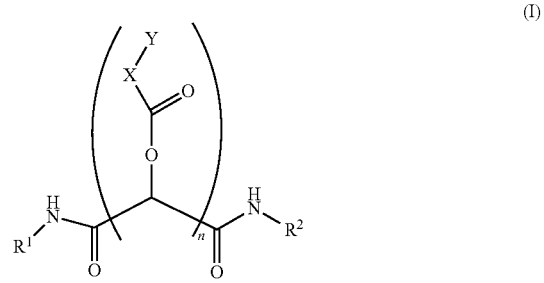

(I)

wherein:
$R^1$ is a polyether or a $(C_1$-$C_6)$alkyl that is optionally substituted with one or more $NR_aR_b$;
$R^2$ is a polyether or a $(C_1$-$C_6)$alkyl that is optionally substituted with one or more $NR_aR_b$;
each X is independently $(C_1$-$C_{20})$alkyl;
$R_a$ and $R_b$ are each independently H or $(C_1$-$C_6)$alkyl;
each Y is independently —$NH_2$, —$N^+(R^c)_3W^-$, —NH—C(=NH)—$NH_2$ or —NH—BOC;
each $R^c$ is independently $(C_1$-$C_6)$alkyl;
W is a counter ion; and
n is 1, 2, 3, 4, 5, 6, 7, or 8;
or a salt thereof.

The invention also provides a compound of formula II:

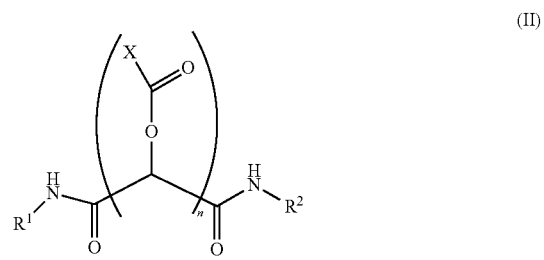

(II)

wherein:
$R^1$ is a polyether or a $(C_1$-$C_6)$alkyl that is substituted with one or more $NR_aR_b$;
$R^2$ is a polyether or a $(C_1$-$C_6)$alkyl that is substituted with one or more $NR_aR_b$;

each X is independently $(C_1-C_{20})$alkyl;

each $R_a$ is independently H or $(C_1-C_6)$alkyl;

each $R_b$ is independently H, $(C_1-C_6)$alkyl or —C(=NH)NH$_2$; and n is 1, 2, 3, 4, 5, 6, 7, or 8;

or a salt thereof.

The invention also provides a method for treating a bacterial infection in a mammal comprising administering to the mammal an effective amount of a compound of formula I, or a pharmaceutically acceptable salt thereof, or a compound of formula II, or a pharmaceutically acceptable salt thereof.

The invention also provides a composition comprising a compound of formula I, or a pharmaceutically acceptable salt thereof, or a compound of formula II, or a pharmaceutically acceptable salt thereof, and a pharmaceutically acceptable vehicle.

The invention also provides a compound of formula I, pharmaceutically acceptable salt thereof, or a compound of formula II, or a pharmaceutically acceptable salt thereof, for the prophylactic or therapeutic treatment of a bacterial infection.

The invention also provides a compound of formula I, pharmaceutically acceptable salt thereof, or a compound of formula II, or a pharmaceutically acceptable salt thereof, for use in medical treatment.

The invention also provides the use of a compound of formula I, or a pharmaceutically acceptable salt thereof, or a compound of formula II, or a pharmaceutically acceptable salt thereof, for the preparation of a medicament for treating a bacterial infection in a mammal.

The invention also provides processes and intermediates disclosed herein that are useful for preparing compounds of formula I, or salts thereof, or compounds of formula II, or salts thereof.

As described in the Examples, experiments measuring the minimum inhibitory concentrations (MIC) and minimum bactericidal concentrations (MBC) against gram positive (S. aureus) and gram negative (E. coli) bacteria were performed using compounds of formula (I) and (II), with certain compounds showing activities comparable to conventional antibiotics. The compounds may be useful as therapeutic agents for clinical applications. The compounds may also be useful to provide an antibiotic effect in soaps and coatings or as delivery agents for other therapeutic or diagnostic agents. The compounds may kill bacterial cells through a membrane disrupting mechanism, which is difficult for bacteria to develop resistance against. Additionally, the compounds are simple and inexpensive to prepare.

DETAILED DESCRIPTION

Compounds of Formula (I)

Figure 1:
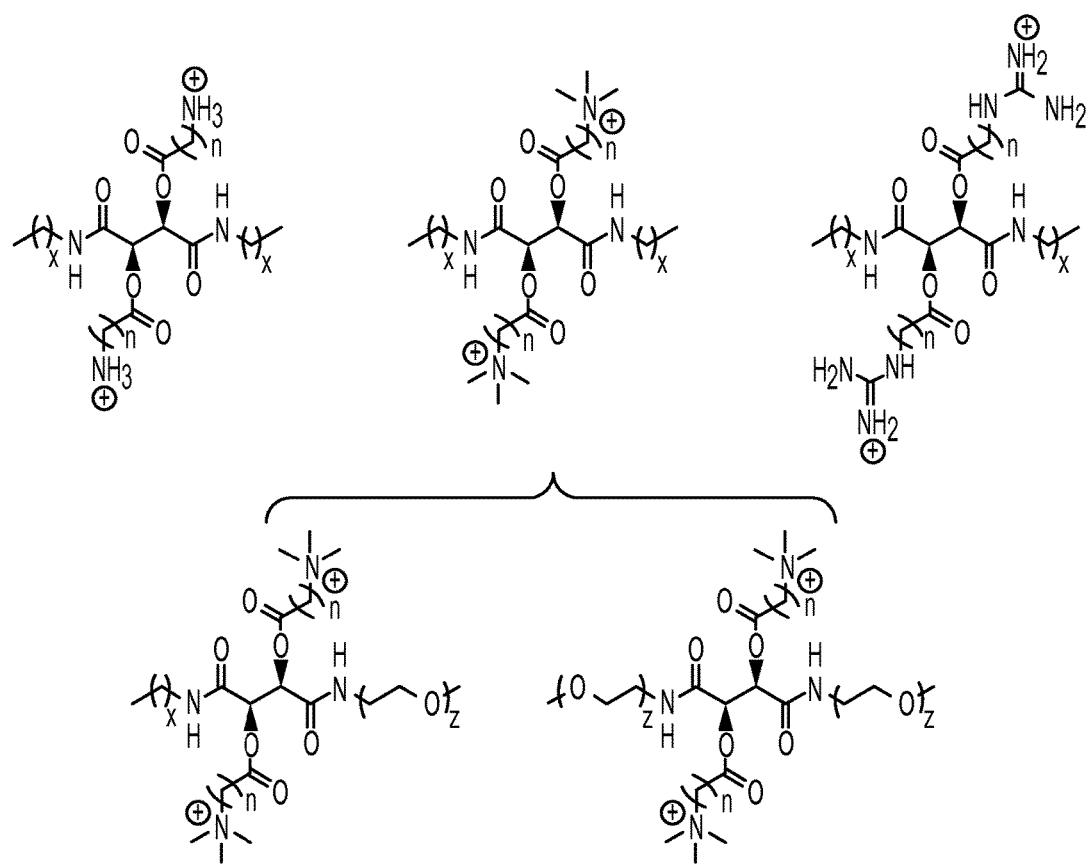
FIG. 1. A representative series of proposed cationic amphiphiles, having a tartaric acid-based backbone, that can be explored for antimicrobial applications. Amphiphiles of different hydrophobicities and different amine-moieties will be investigated. Examples of PEGylation strategies are presented for one amphiphile structure.

Accordingly, the invention provides a compound of formula I:

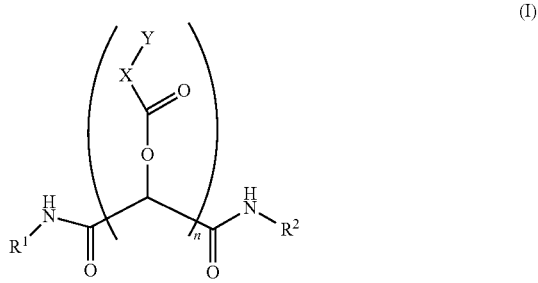

wherein:

$R^1$ is a polyether or a $(C_1-C_6)$alkyl that is optionally substituted with one or more $NR_aR_b$;

$R^2$ is a polyether or a $(C_1-C_6)$alkyl that is optionally substituted with one or more $NR_aR_b$;

each X is independently $(C_1-C_{20})$alkyl;

$R_a$ and $R_b$ are each independently H or $(C_1-C_6)$alkyl;

each Y is independently —$NH_2$, —$N^+(R^c)_3W^-$, —NH—C(=NH)—$NH_2$ or —NH—BOC;

each $R^c$ is independently $(C_1-C_6)$alkyl;

W is a counter ion; and n is 1, 2, 3, 4, 5, 6, 7, or 8;

or a salt thereof.

In certain embodiments, each Y is independently —$NH_2$.

In certain embodiments, each Y is independently —$N^+(R^c)_3W^-$.

In certain embodiments, each Y is independently —NH—C(=NH)—$NH_2$.

In certain embodiments, each Y is independently —NH—BOC.

In certain embodiments, each $R_a$ is independently H. In certain embodiments, each $R_a$ is independently $(C_1-C_6)$alkyl.

In certain embodiments, each $R_b$ is independently H. In certain embodiments, each $R_b$ is independently $(C_1-C_6)$alkyl.

In certain embodiments, n is 2. In certain embodiments, n is 3. In certain embodiments, n is 4. In certain embodiments, n is 5.

In certain embodiments, a compound of formula I is a compound of formula Ic:

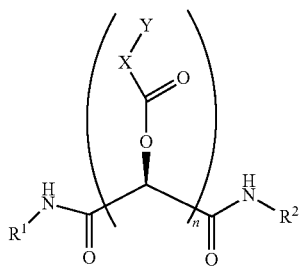

(Ic)

wherein:

$R^1$ is a polyether or a $(C_1-C_6)$alkyl that is optionally substituted with one or more $NR_aR_b$;

$R^2$ is a polyether or a $(C_1-C_6)$alkyl that is optionally substituted with one or more $NR_aR_b$;

each X is independently $(C_1-C_{20})$alkyl;

$R_a$ and $R_b$ are each independently H or $(C_1-C_6)$alkyl;

each Y is independently —$NH_2$, —$N^+(R^c)_3W^-$, —NH—C(=NH)—$NH_2$ or —NH—BOC;

each $R^c$ is independently $(C_1-C_6)$alkyl;

W is a counter ion; and n is 1, 2, 3, 4, 5, 6, 7, or 8;

or a salt thereof.

In certain embodiments, a compound of formula I is a compound of formula Ib:

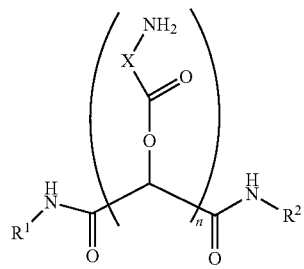

(Ib)

wherein:

$R^1$ is a polyether or a $(C_1-C_6)$alkyl; and $R^2$ is a polyether or a $(C_1-C_6)$alkyl;

or a salt thereof.

In certain embodiments, a compound of formula I is a compound of formula Ib':

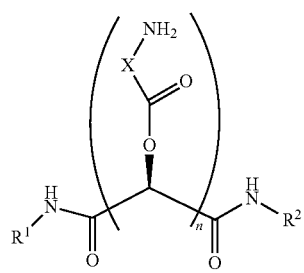

(Ib')

wherein:

$R^1$ is a polyether or a $(C_1-C_6)$alkyl; and $R^2$ is a polyether or a $(C_1-C_6)$alkyl;

or a salt thereof.

In certain embodiments, a compound of formula I is a compound of formula Ia:

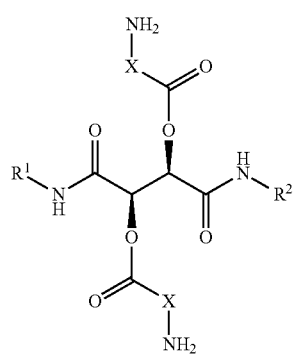

(Ia)

or a salt thereof.

In certain embodiments, a compound of the invention is selected from:
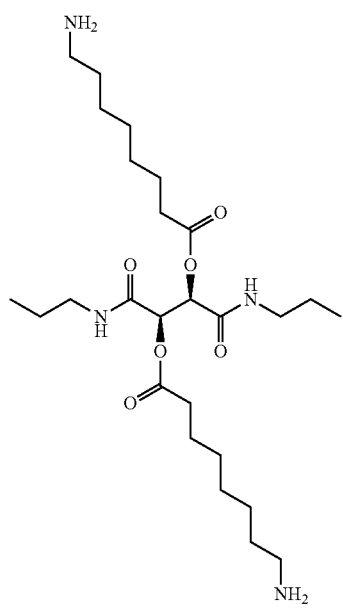
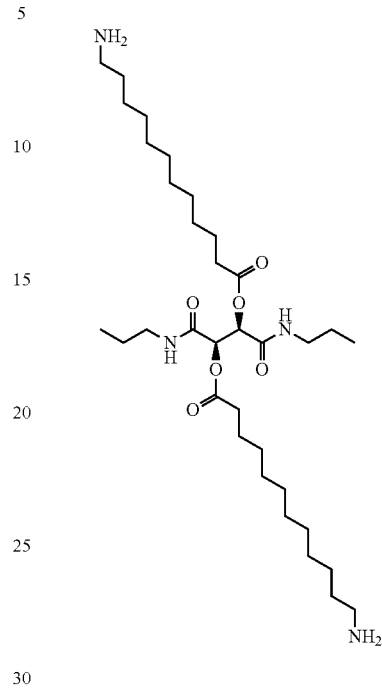
and salts thereof.
In certain embodiments, a compound of the invention is selected from:
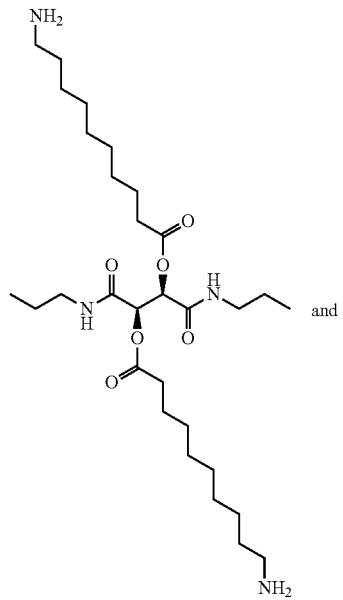
and
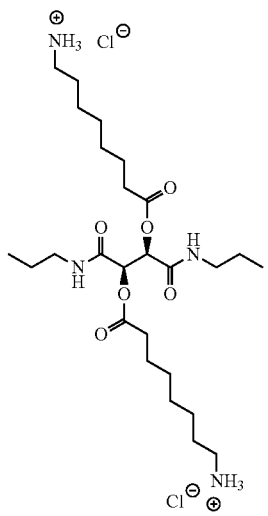

-continued

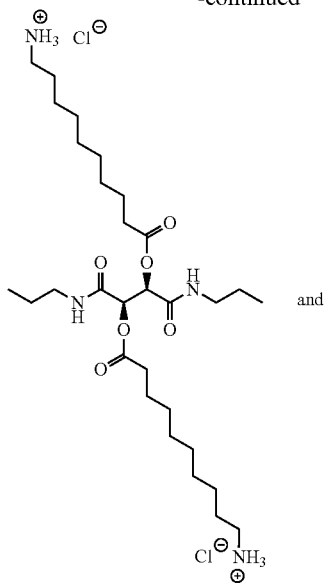

and

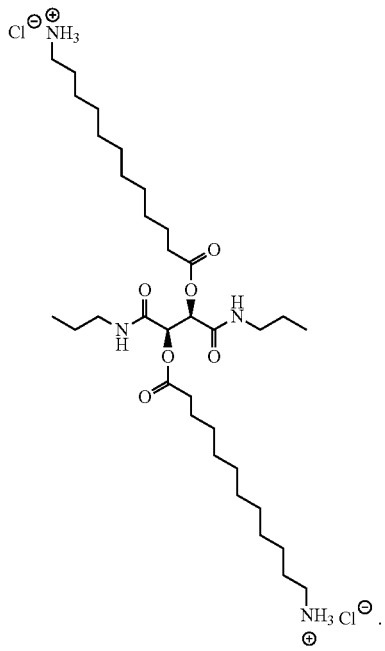 [SMILES: [Cl-] ; CCCNC(=O)[C@H](OC(=O)CCCCCCCCCCC[NH3+])[C@@H](OC(=O)CCCCCCCCCCC[NH3+])C(=O)NCCC ; [Cl-]]

Compounds of Formula (II)

The invention also provides a compound of formula II:

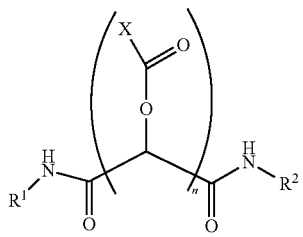
(II)

wherein:
R¹ is a polyether or a $(C_1-C_6)$alkyl that is substituted with one or more $NR_aR_b$;
R² is a polyether or a $(C_1-C_6)$alkyl that is substituted with one or more $NR_aR_b$;
each X is independently $(C_1-C_{20})$alkyl;
each $R_a$ is independently H or $(C_1-C_6)$alkyl;
each $R_b$ is independently H, $(C_1-C_6)$alkyl or —C(=NH)NH₂; and
n is 1, 2, 3, 4, 5, 6, 7, or 8;
or a salt thereof.

In certain embodiments, each $R_a$ is independently H. In certain embodiments, each $R_a$ is independently $(C_1-C_6)$alkyl.

In certain embodiments, each $R_b$ is independently H. In certain embodiments, each $R_b$ is independently $(C_1-C_6)$alkyl. In certain embodiments, each $R_b$ is independently —C(=NH)NH₂.

In certain embodiments, n is 2. In certain embodiments, n is 3. In certain embodiments, n is 4. In certain embodiments, n is 5.

In certain embodiments, a compound of formula II is a compound of formula IIa:

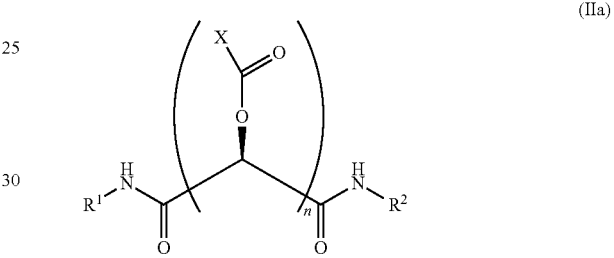
(IIa)

wherein:
R¹ is a polyether or a $(C_1-C_6)$alkyl that is substituted with one or more $NR_aR_b$;
R² is a polyether or a $(C_1-C_6)$alkyl that is substituted with one or more $NR_aR_b$;
each X is independently $(C_1-C_{20})$alkyl;
$R_a$ is each independently H or $(C_1-C_6)$alkyl;
$R_b$ is each independently H, $(C_1-C_6)$alkyl or —C(=NH)NH₂; and
n is 1, 2, 3, 4, 5, 6, 7, or 8;
or a salt thereof.

In certain embodiments, a compound of formula II is a compound of formula IIb:

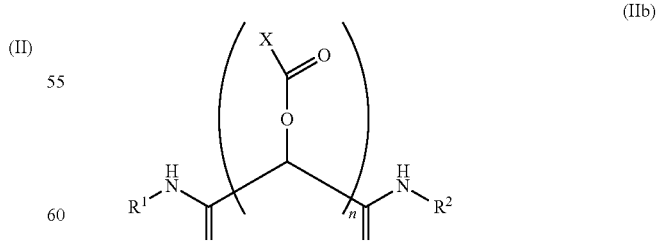
(IIb)

wherein:
R¹ is a polyether or a $(C_1-C_6)$alkyl that is substituted with one or more $NR_aR_b$;

$R^2$ is a polyether or a $(C_1$-$C_6)$alkyl that is substituted with one or more $NR_aR_b$;

each $R_a$ is H; and each $R_b$ is H;

or a salt thereof.

In certain embodiments, a compound of formula II is a compound of formula IIc:

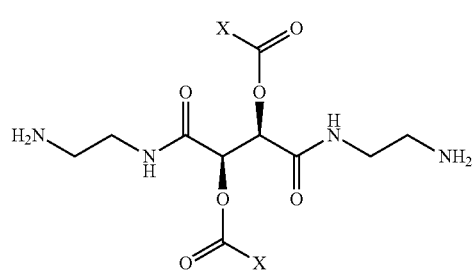

(IIc)

or a salt thereof.

In certain embodiments, a compound of the invention is selected from:

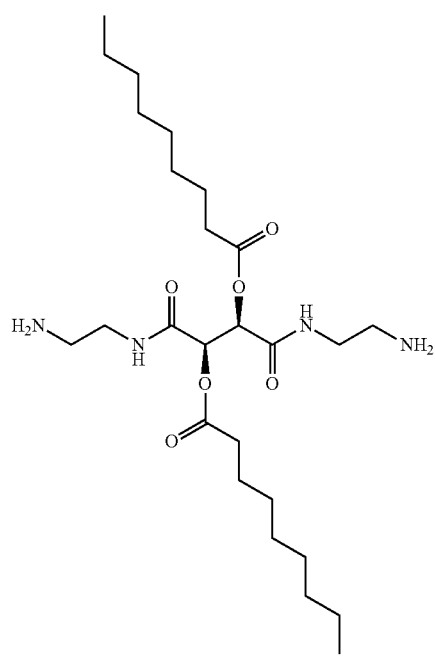

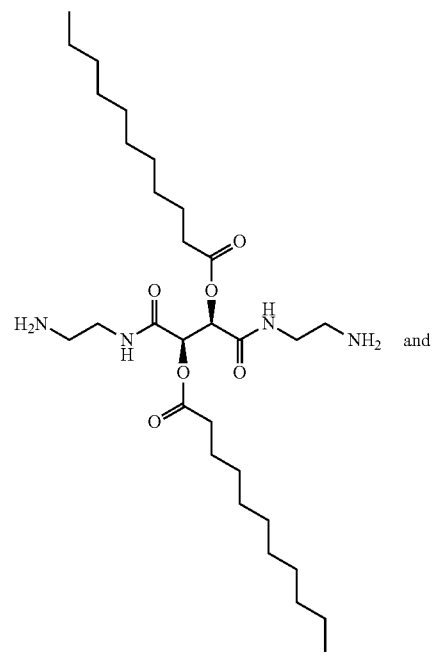

and

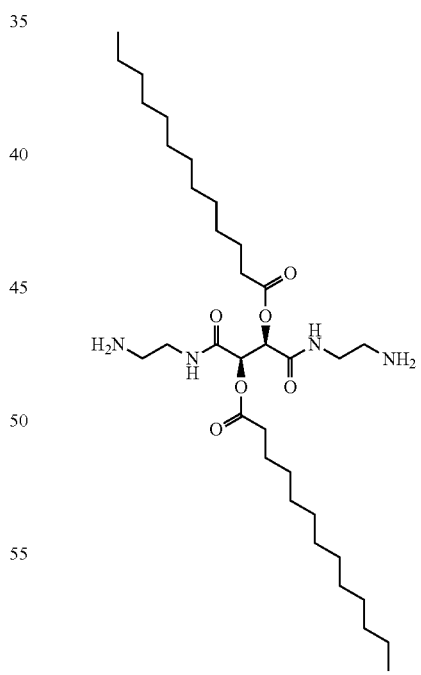

and salts thereof.

In certain embodiments, a compound of the invention is selected from:

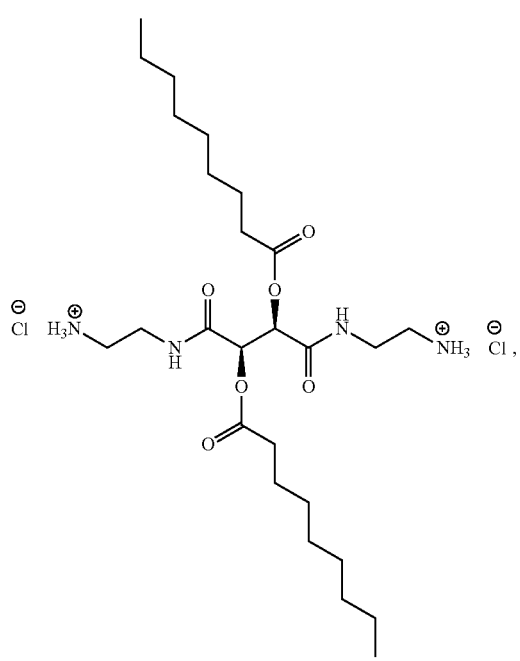

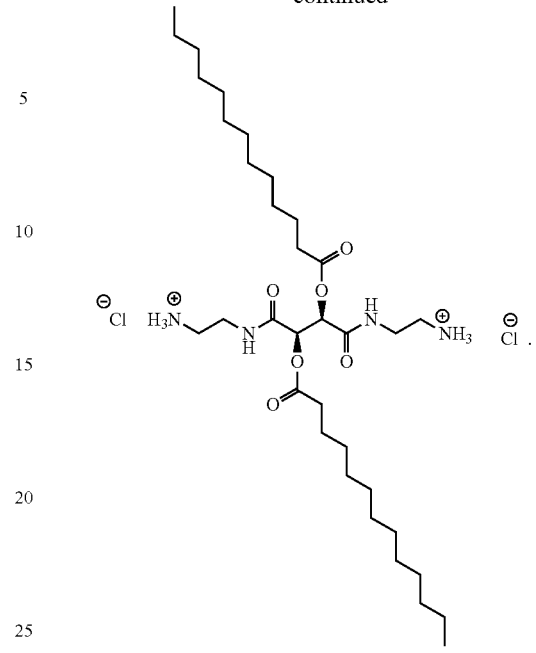

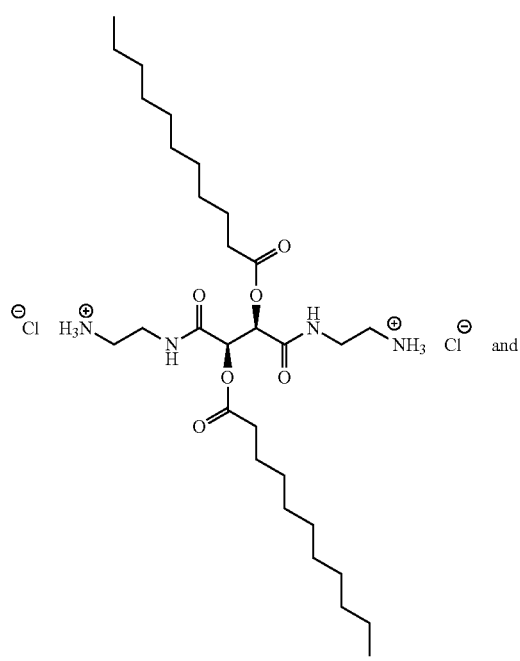

Variables "$R^1$" and "$R^2$"

As described herein, certain embodiments of the invention provide compounds of formula I, wherein $R^1$ is a polyether or a $(C_1\text{-}C_6)$alkyl that is optionally substituted with one or more $NR_aR_b$; and $R^2$ is a polyether or a $(C_1\text{-}C_6)$alkyl that is optionally substituted with one or more $NR_aR_b$. Certain embodiments of the invention also provide compounds of formula II, wherein $R^1$ is a polyether or a $(C_1\text{-}C_6)$alkyl that is substituted with one or more $NR_aR_b$; and $R^2$ is a polyether or a $(C_1\text{-}C_6)$alkyl that is substituted with one or more $NR_aR_b$.

In certain embodiments, $R^1$ is a $(C_1\text{-}C_6)$alkyl that is optionally substituted with one or more $NR_aR_b$.

In certain embodiments, $R^1$ is a $(C_1\text{-}C_6)$alkyl that is substituted with one or more $NR_aR_b$.

In certain embodiments, $R^1$ is methyl, ethyl, propyl, isopropyl, butyl, isobutyl, or sec-butyl, optionally substituted with one or more $NR_aR_b$.

In certain embodiments, $R^1$ is methyl, ethyl, propyl, isopropyl, butyl, isobutyl, or sec-butyl.

In certain embodiments, $R^1$ is propyl.

In certain embodiments, $R^1$ is a polyether. As used herein, the term polyether includes poly(alkylene oxides) having between about 2 and about 150 repeating units. Typically, the poly(alkylene oxides) have between about 50 and about 115 repeating units. The alkylene oxide units contain from 2 to 10 carbon atoms and may be straight chained or branched. Preferably, the alkylene oxide units contain from 2 to 10 carbon atoms. Poly(ethylene glycol) (PEG) is a specific example of a poly(alkylene oxide). Alkoxy-, amino-, carboxy-, and sulfo-terminated poly(alkylene oxides) are also examples, with methoxy-terminated poly(alkylene oxides) being a specific example.

In one embodiment the polyether has the following structure:

$$R_5\text{—}(R_6\text{—}O\text{—})_a\text{—}R_6\text{—}$$

wherein $R_5$ is a 1 to 20 carbon straight-chain or branched alkyl group, —OH, —$OR_7$, —$NH_2$, —$NHR_7$, —$NHR_7R_8$, —$CO_2H$, —$SO_3H$ (sulfo), —$CH_2$—OH, —$CH_2$—$OR_7$, —CH$_2$—O—CH$_2$—R$_7$, —CH$_2$—NH$_2$, —CH$_2$—NHR$_7$, —CH$_2$—NR$_7$R$_8$, —CH$_2$CO$_2$H, —CH$_2$SO$_3$H, or —O—C(=O)—CH$_2$—CH$_2$—C(=O)—O—;

R$_6$ is a 1 to 10 carbon straight-chain or branched divalent alkylene group;

each R$_7$ and R$_8$ is independently a 1 to 6 carbon straight-chain or branched alkylene group; and a is an integer from 2 to 150, inclusive.

In certain embodiments, a is an integer from 20 to 140, inclusive. In certain embodiments, a is an integer from 50 to 130, inclusive. In certain embodiments, a is an integer from 75 to 130, inclusive. In certain embodiments, a is an integer from 100 to 130, inclusive. In certain embodiments, a is 113.

In another embodiment the polyether is methoxy terminated poly(ethylene glycol).

In certain embodiments, R$^2$ is a (C$_1$-C$_6$)alkyl that is optionally substituted with one or more NR$_a$R$_b$.

In certain embodiments, R$^2$ is a (C$_1$-C$_6$)alkyl that is substituted with one or more NR$_a$R$_b$.

In certain embodiments, R$^2$ is methyl, ethyl, propyl, isopropyl, butyl, isobutyl, or sec-butyl, optionally substituted with one or more NR$_a$R$_b$.

In certain embodiments, R$^2$ is methyl, ethyl, propyl, isopropyl, butyl, isobutyl, or sec-butyl.

In certain embodiments, R$^2$ is propyl.

In certain embodiments, R$^2$ is a polyether.

Variable "X"

As described herein, in certain embodiments of compounds of formula I and II, each X is independently (C$_1$-C$_{20}$)alkyl. In certain embodiments, each X is independently (C$_2$-C$_{20}$)alkyl. In certain embodiments, each X is independently (C$_4$-C$_{12}$)alkyl. In certain embodiments, each X is independently (C$_6$)alkyl. In certain embodiments, each X is independently (C$_7$)alkyl. In certain embodiments, each X is independently (C$_8$)alkyl. In certain embodiments, each X is independently (C$_9$)alkyl. In certain embodiments, each X is independently (C$_{10}$)alkyl. In certain embodiments, each X is independently (C$_{11}$)alkyl. In certain embodiments, each X is independently (C$_{12}$)alkyl.

Compositions

As described herein, compounds of the invention may be formulated as compositions. Accordingly, certain embodiments of the invention provide a pharmaceutical composition comprising a compound of formula I, or a pharmaceutically acceptable salt thereof, or a compound of formula II, or a pharmaceutically acceptable salt thereof, and a pharmaceutically acceptable carrier.

Certain other embodiments provide a soap comprising a compound of formula I, or a salt thereof, or a compound of formula II, or a salt thereof.

Certain embodiments of the invention provide a coating or paint comprising a compound of formula I, or a salt thereof, or a compound of formula II, or a salt thereof.

Certain embodiments of the invention provide composition comprising a compound of formula I, or a salt thereof, or a compound of formula II, or a salt thereof, and a therapeutic or diagnostic agent.

Methods of Use

Certain embodiments of the invention provide a method for treating a bacterial infection in a mammal comprising administering to the mammal an effective amount of a compound as described herein, or a pharmaceutically acceptable salt thereof.

In certain embodiments, the bacterial infection is a Gram-negative bacterial strain infection.

In certain embodiments, the Gram-negative bacterial strain is selected from the group consisting of *Escherchia coli, Caulobacter crescentus, Pseudomonas aeruginosa, Agrobacterium tumefaciens, Branhamella catarrhalis, Citrobacter diversus, Enterobacter aerogenes, Enterobacter cloacae, Enterobacter sakazakii, Enterobacter asburiae, Pantoea agglomerans, Klebsiella pneumoniae, Klebsiella oxytoca, Klebsiella rhinoscleromatis, Proteus mirabilis, Salmonella typhimurium, Salmonella enteriditis, Serratia marcescens, Shigella sonnei, Neisseria gonorrhoeae, Acinetobacter baumannii, Acinetobacter calcoaceticus, Acinetobacter lwoffi, Salmonella enteriditis, Fusobacterium nucleatum, Veillonella parvula, Bacteroides forsythus, Actinobacillus actinomycetemcomitans, Aggregatibacter actinomycetemcomitans, Porphyromonas gingivalis, Helicobacter pylori, Francisella tularensis, Yersinia pestis, Borrelia burgdorferi, Neisseria meningitides, Burkholderia cepacia, Brucella neotomae, Legionella pneumophila, Y pseudotuberculosis*, and *Haemophilus influenzae*.

In certain embodiments, the bacterial infection is a Gram-negative bacterial strain infection and a compound of formula II is administered to the mammal.

In certain embodiments, the bacterial infection is a Gram-positive bacterial strain infection.

In certain embodiments, the Gram-positive bacterial strain is selected from the group consisting of *Staphylococcus aureus, Staphylococcus epidermidis, Staphylococcus saprophyticus, Streptococcus pyogenes, Streptococcus faecalis, Enterococcus faecalis, Enterococcus faecium, Bacillus subtilis, Micrococcus luteus, Mycobacterium tuberculosis, Bacillus anthracis, Bacillus cereus, Clostridium difficile, Propionibacterium acnes, Streptococcus mutans, Actinomyces viscosus, Actinomyces naeslundii, Streptococcus sanguis, Streptococcus pneumoniae, Listeria monocytogenes* and *Streptococcus salivarius*.

In certain embodiments, the bacterial infection is a Gram-positive bacterial strain infection and a compound of formula I is administered to the mammal.

In certain embodiments, the bacterial infection is a Gram-positive bacterial strain infection and a compound of formula II is administered to the mammal.

In certain embodiments, the Gram-positive bacterial strain is *Mycobacterium tuberculosis*.

In certain embodiments, the bacterial infection is tuberculosis.

Certain embodiments of the invention provide a compound of formula I, or a pharmaceutically acceptable salt thereof, or a compound of formula II, or a pharmaceutically acceptable salt thereof, for the prophylactic or therapeutic treatment of a bacterial infection.

Certain embodiments of the invention provide a compound of formula I, or a pharmaceutically acceptable salt thereof, or a compound of formula II, or a pharmaceutically acceptable salt thereof, for use in medical treatment.

Certain embodiments of the invention provide the use of a compound of formula I, or a pharmaceutically acceptable salt thereof, or a compound of formula II, or a pharmaceutically acceptable salt thereof, for the preparation of a medicament for treating a bacterial infection in a mammal.

Certain Definitions

The following definitions are used, unless otherwise described: halo is fluoro, chloro, bromo, or iodo. Alkyl, alkoxy, alkenyl, alkynyl, etc. denote both straight and branched groups; but reference to an individual radical such as propyl embraces only the straight chain radical, a branched chain isomer such as isopropyl being specifically referred to.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

Specific values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl.

As used herein the term "Boc" refers to —C(=O)OC(CH$_3$)$_3$.

As used herein the term "salt" includes base addition, acid addition and quaternary salts. Compounds of the invention which are acidic can form salts, including pharmaceutically acceptable salts, with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris(hydroxymethyl)amino-methane, L-arginine, L-lysine, N-ethyl piperidine, dibenzylamine and the like. Those compounds which are basic can form salts, including pharmaceutically acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic, p-toluenesulphonic, benzoic, benzenesulfonic, glutamic, lactic, and mandelic acids and the like. For a review on suitable salts, see Handbook of Pharmaceutical Salts: Properties, Selection, and Use by Stahl and Wermuth (Wiley-VCH, Weinheim, Germany, 2002).

In cases where compounds are sufficiently basic or acidic, a salt of a compound of formula I or II can be useful as an intermediate for isolating or purifying a compound of formula I or II. Additionally, administration of a compound of formula I as a pharmaceutically acceptable acid or base salt may be appropriate. Pharmaceutically acceptable salts may be obtained using standard procedures well known in the art.

Administration of Compounds of Formula I or II

As described herein, a compound of formula I, or a pharmaceutically acceptable salt thereof, or a compound of formula II, or a pharmaceutically acceptable salt thereof, can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I or II to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I or II can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Certain Methods for Preparing Compounds of Formula I or II

Figure 2:
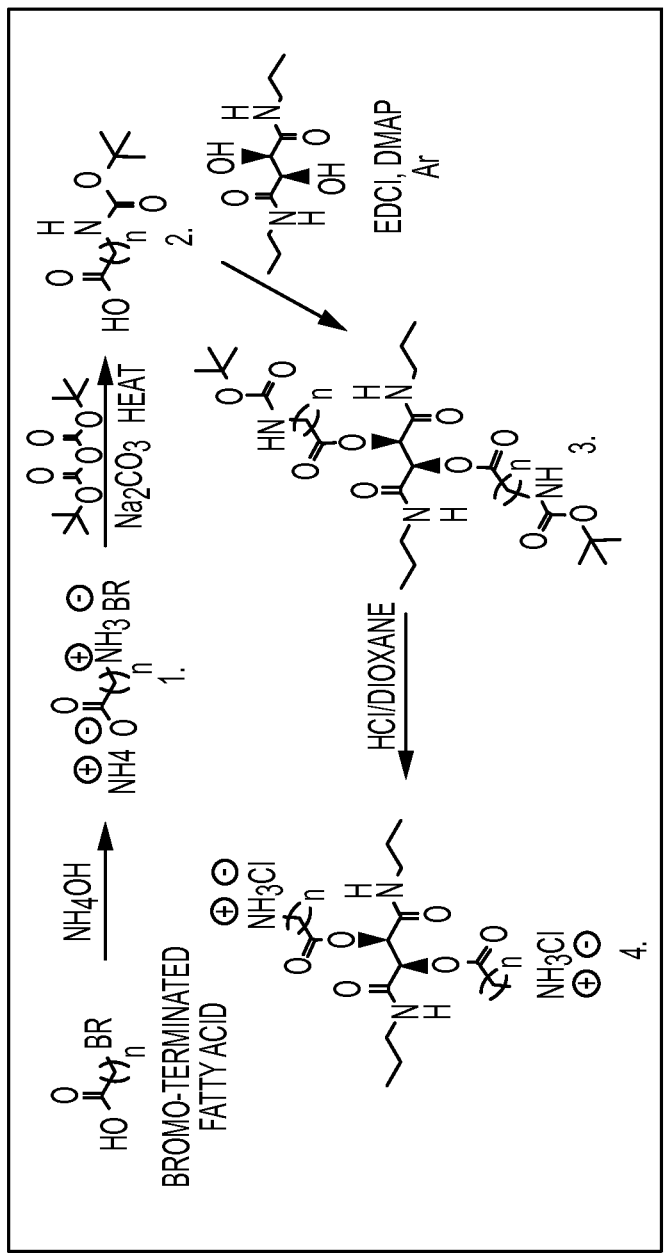
FIG. 2. Synthetic scheme used to synthesize tartaric acid-based amphiphiles containing primary amine-terminated aliphatic chains.
Figure 3:
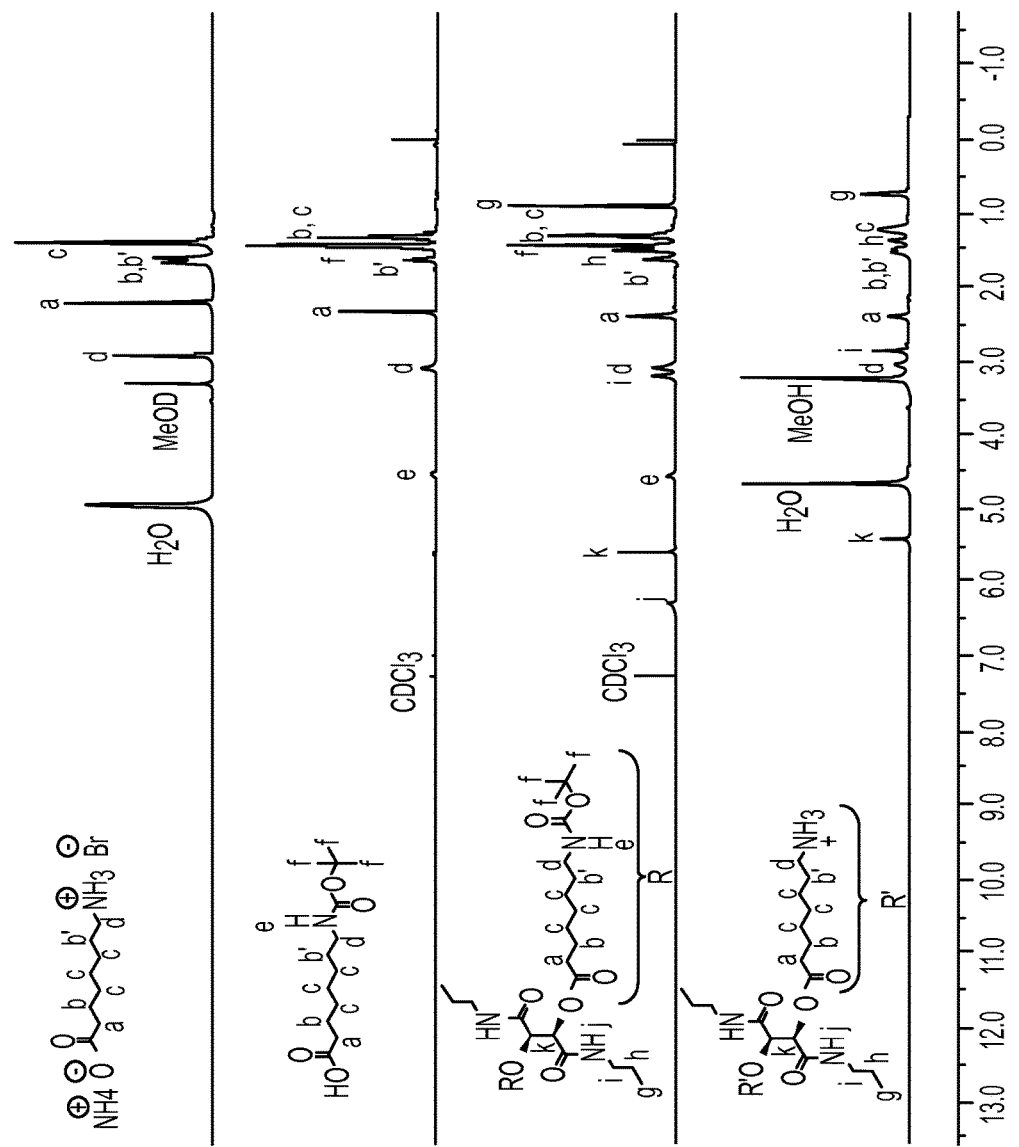
FIG. 3. Proton nuclear magnetic resonance spectra for synthesis of a tartaric-acid based amphiphile with primary amine-terminated aliphatic arms.
Figure 4:
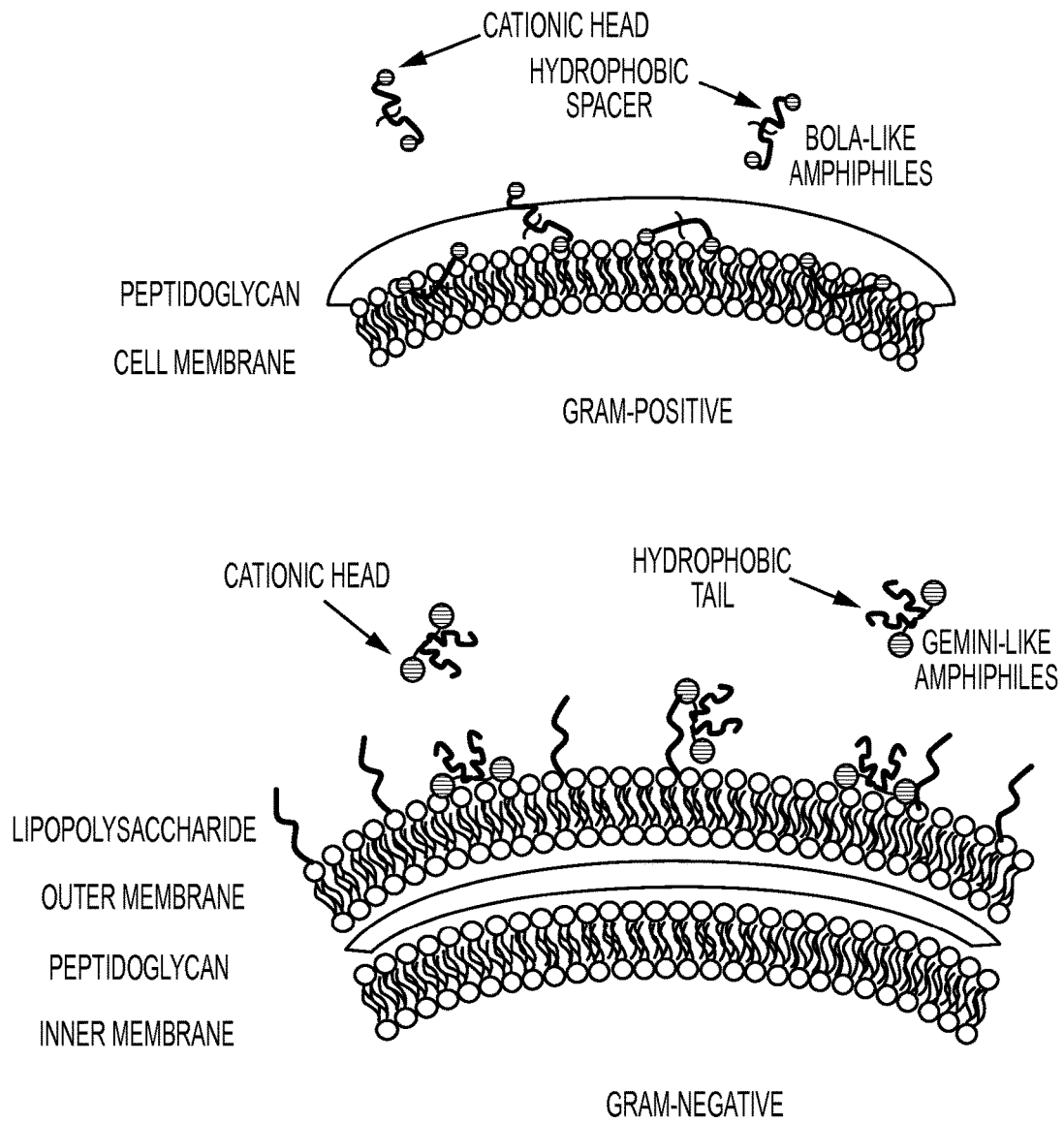
FIG. 4. Proposed interaction between bola-like amphiphiles and gram-positive bacteria (top panel) and gemini-like amphiphiles and gram-negative bacteria (bottom panel).

Generally, compounds of formula I and II, as well as synthetic intermediates that can be used for preparing compounds of formula I and II, can be prepared as illustrated in FIG. 2 and in the following Schemes and Examples. It is understood that variable groups shown in the Schemes below (e.g. $R^1$, $R^2$, X and $X_1$) can represent the final corresponding groups present in a compound of formula I or II or that these groups can represent groups that can be converted to the final corresponding groups present in a compound of formula I or II at a convenient point in a synthetic sequence. For example, in the Schemes below, the variable groups can contain one or more protecting groups that can be removed at a convenient point in a synthetic sequence to provide the final corresponding groups in the compound of formula I or II. Processes for preparing compounds of formula I or II are provided as further embodiments.

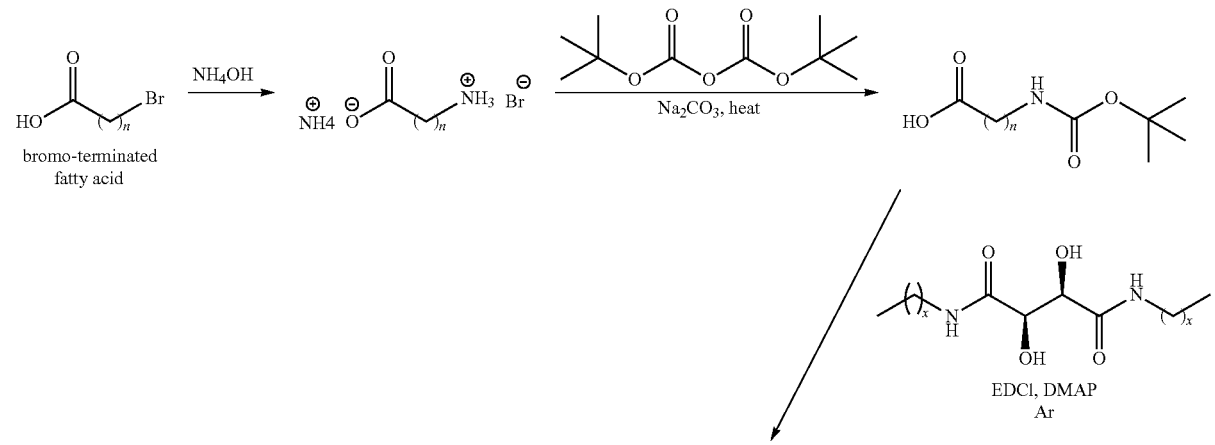

Scheme 1.

-continued
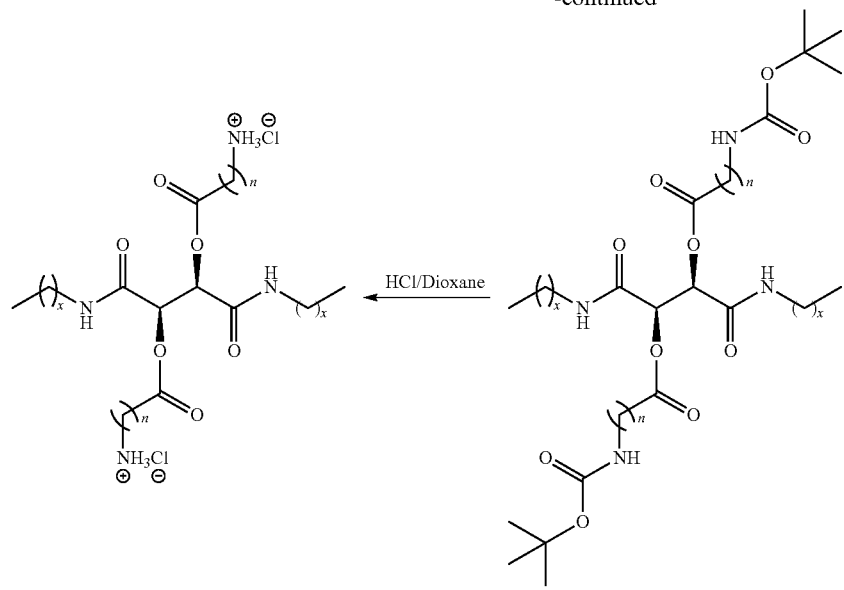

Scheme 2: PEGylated derivatives
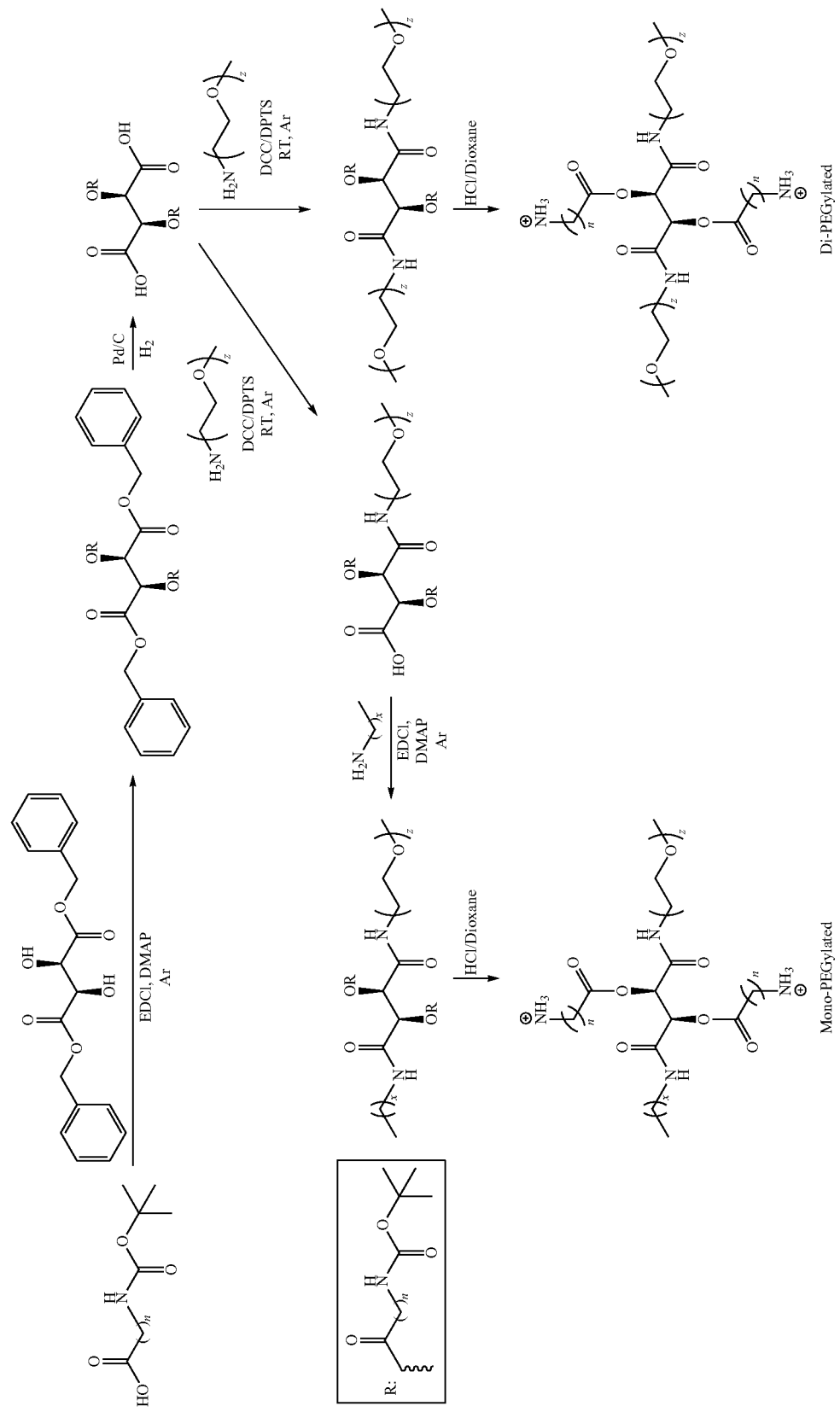

Scheme 3: Various Synthetic Pathways
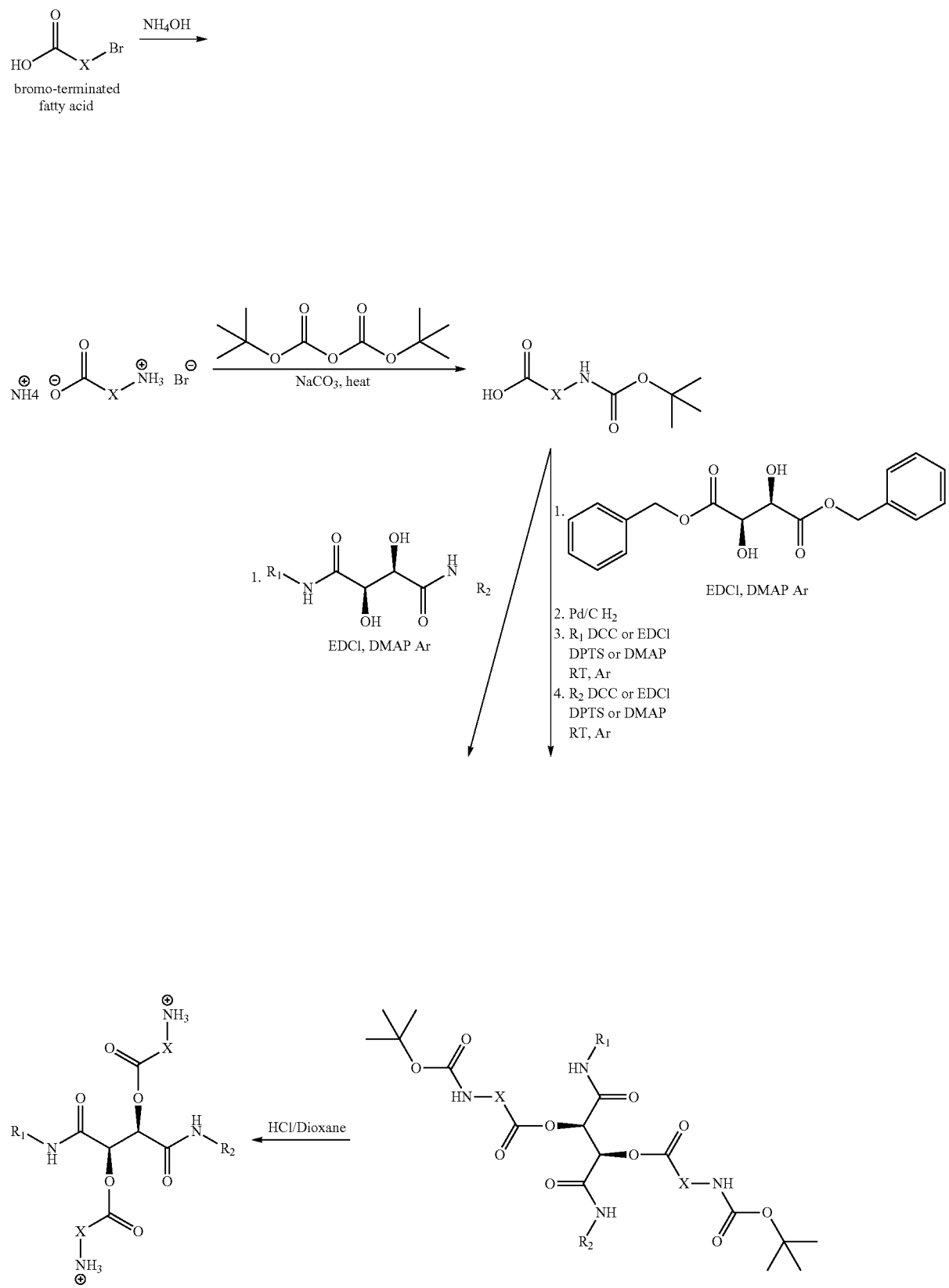

Scheme 4: Generation of Certain Amine Moieties
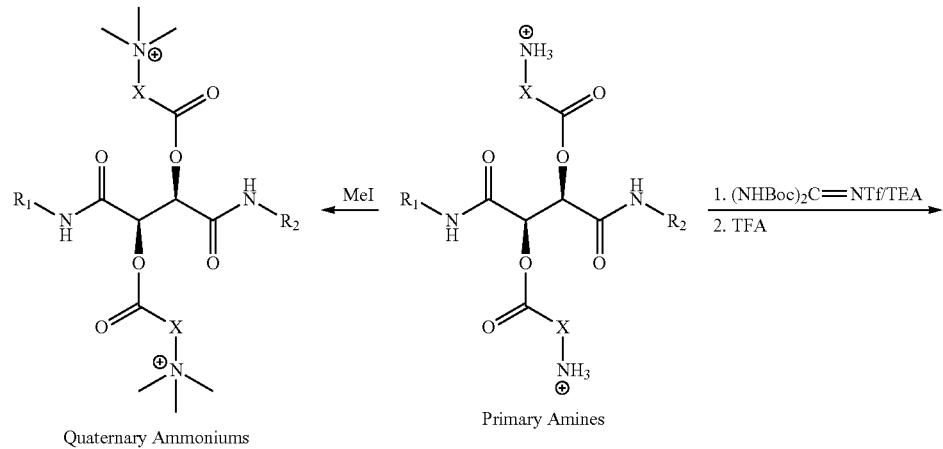
Quaternary Ammoniums
Primary Amines
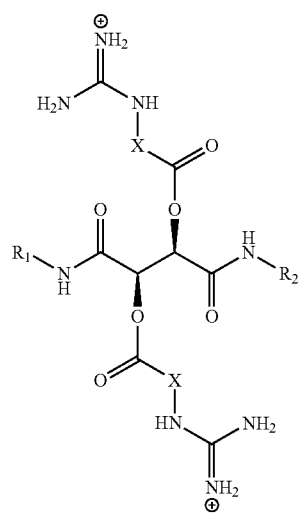
Guanidiniums
Scheme 5
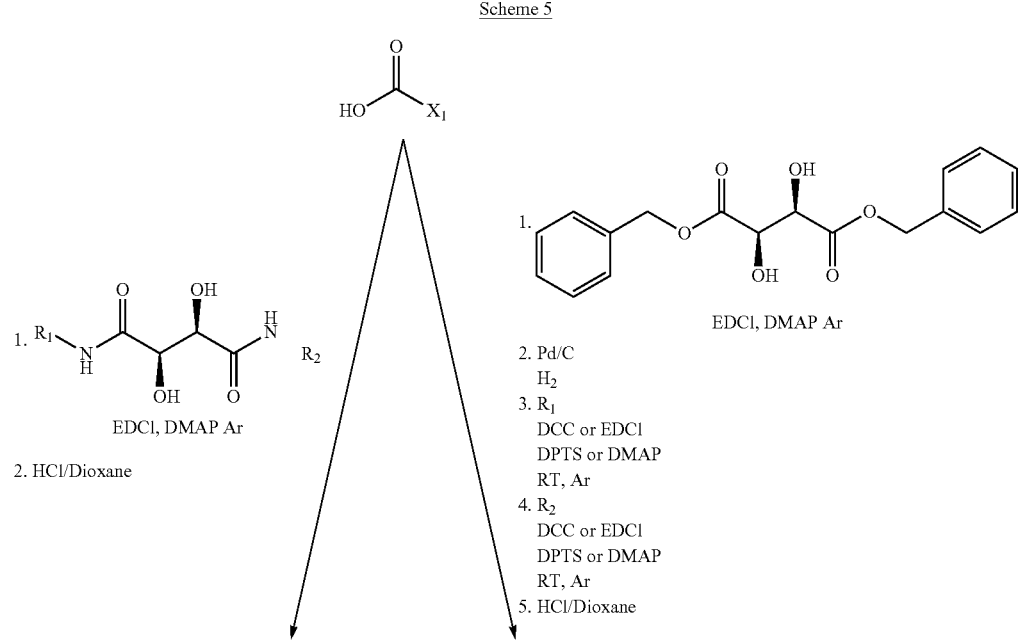
1. $R_1$
   EDCl, DMAP Ar
2. HCl/Dioxane
1.
2. Pd/C
   $H_2$
3. $R_1$
   DCC or EDCl
   DPTS or DMAP
   RT, Ar
4. $R_2$
   DCC or EDCl
   DPTS or DMAP
   RT, Ar
5. HCl/Dioxane
EDCl, DMAP Ar -continued

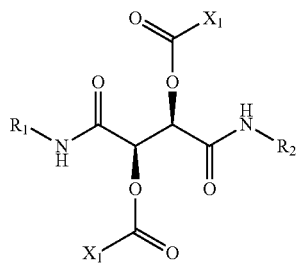

In certain embodiments, $X_1$ in Scheme 5 above may be an aliphatic arm of one or more methlylenes, which is boc-protected amino terminated or amine-terminated.

The antibiotic properties of a compound may be determined using pharmacological models which are well known to the art, or using assays described in the Examples below (e.g., Test A).

The invention will now be illustrated by the following non-limiting Examples.

Example 1

Test A.

MIC/MBC studies were conducted according to a modified literature procedure (LaDow J E, et al. European Journal of Medicinal Chemistry. 46 (2011) 4219-4226). In brief, stock amphiphile solutions were made in 1 mL double-distilled water (0.1M C8 and C10; 0.02M C12), filter sterilized, and sonicated for five minutes. Stocks were then diluted 100× in tryptic soy broth and vortexed. This broth was serially diluted in fresh broth and 100 μL "doped" broth was transferred to 96-well microtiter plate. $10^6$ Cfu/mL inoculums were prepared for *E. coli* and *S. aureus*. 100 μL inoculum was added to the wells. Plates were put on a shaker for 5 minutes to mix inoculum and broth. Plates were incubated at 37° C. overnight. Wells were visually analyzed the next day by growth or no growth. After MICs were determined, aliquots were taken from each well, plated, and incubated to determine the MBC values for each compound. MBC values were defined as killing of ≥99.9% of the organisms, which corresponds to a 3-log reduction.

Data for the following representative compounds of formula (I) in Test A is provided in Tables 1 and 2 below.

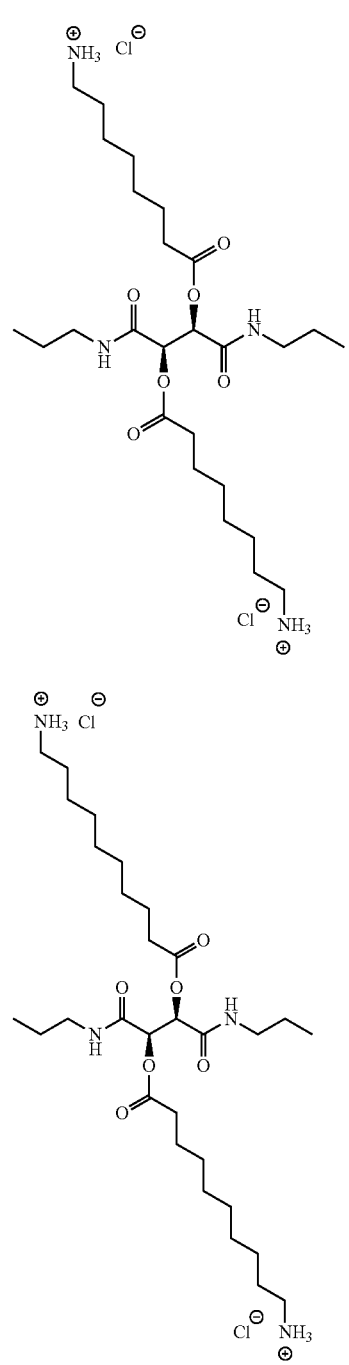

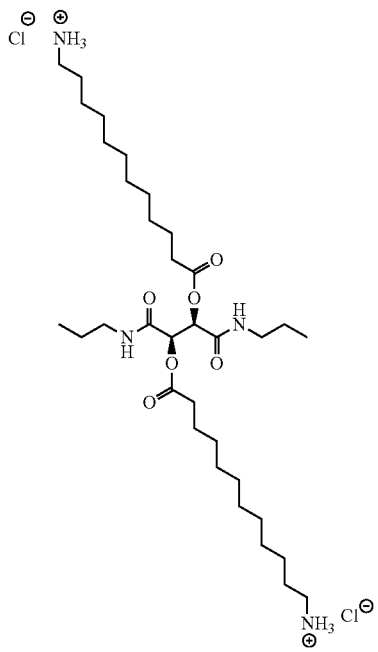

C12

TABLE 1

MICs and MBCs (mM) of Amphiphiles*

| Amphiphile | S. aureus | E. coli |
|---|---|---|
| C8 | 0.5 (0.5) | 1 (1) |
| C10 | 0.125 (0.25) | 0.5 (0.5) |
| C12 | 0.025 (0.05) | 0.4 (0.4) |
| Streptomycin Sulfate (µg/mL) | <100 (<100) | <100 (<100) |

*Data represented in MIC (MBC) format.

TABLE 2

MICs and MBCs (µg/mL) of Amphiphiles*

| Amphiphile | S. aureus | E. coli |
|---|---|---|
| C8 | 294 (294) | 588 (588) |
| C10 | 80.5 (171) | 322 (322) |
| C12 | 17.5 (35.0) | 280 (280) |
| Streptomycin Sulfate | <100 (<100) | <100 (<100) |

*Data represented in MIC (MBC) format.
MIC defined as inhibition of growth determined by the unaided eye.
MBC is defined as killing of ≥99.9% of the organisms, which corresponds to a 3-log reduction.

These results demonstrate that compounds of the invention possess antibiotic properties.

Materials and Methods

Cationic amphiphiles (8C, 10C and 12C) were synthesized according to a procedure similar to the procedure illustrated in FIG. 2. The following synthesis is presented for a 1 g scale. Bromo-terminated fatty acids containing 8, 10, 12 carbons were stirred in concentrated ammonium hydroxide solution (5, 50, or 100 mL with increasing carbon numbers) for 1-2 days. Pure 1 was then isolated in vacuo. 1 (1 eq) was suspended in a 1:1 mixture (9-18 mL each) of dioxane and 10% aqueous sodium carbonate solution. The reaction mixture was warmed to 30° C. and additional water added if necessary to aid with stirring. Boc anhydride (1.1 eq) was then added and the reaction mixture heated to reflux temperatures (65° C.) and stirred overnight. The reaction mixture was concentrated in vacuo, reconstituted in 1N hydrochloric acid (HCl, 50 mL) and diethyl ether (15 mL), and extracted with diethyl ether (4×50 mL). The combined ether layers were washed with brine (50 mL), dried over magnesium sulfate, and concentrated in vacuo to obtain 2. Next, 2 (2.2 eq), N,N-propyltartramide (1 eq), and catalytic dimethylaminopyridine (0.42 eq) were dissolved in dichloromethane (DCM, 40-50 mL) and dimethyl formamide (15-25 mL) under argon. Upon complete dissolution of all reagents, 1-ethyl-3-(3-dimethylaminopropyl)carbodiimide (4.2 eq) was added as a coupling reagent and the reaction stirred overnight. The reaction mixture was concentrated in vacuo and reconstituted in DCM (50 mL). This solution was washed with aqueous solutions of 10% potassium bisulfite (3×50 mL), saturated sodium bicarbonate (3×50 mL) and brine (50 mL). The organic layer was then dried over $MgSO_4$ and 3 isolated in vacuo. To obtain the final cationic products (4; 8C, 10C, and 12C), an anhydrous solution of 4M HCl in dioxane (40 eq) was cooled to 0° C. under argon. 3 (1 eq) was added and the reaction stirred at 0° C. under argon for 30 minutes. The reaction mixture was warmed to room temperature and stirred an additional three hours, after which the reaction mixture was concentrated in vacuo. The crude product was dissolved in minimal methanol and pure product (4) precipitated with diethyl ether (400 mL). 4 was isolated via centrifugation (3500 rpm, 5 minutes) and the ether decanted.

8C. Off-white solid. $^1$H-NMR (400 MHz, $CD_3OD$): δ 8.25 (b, 2H), 5.57 (s, 2H), 3.15 (m, 4H), 2.92 (t, 4H), 2.48 (m, 4H), 1.64 (m, 8H), 1.51 (m, 4H), 1.39 (b, 12H), 0.90 (t, 6H). $^{13}$C-NMR (500 MHz, $CD_3OD$): δ 172.65, 167.62, 72.58, 41.18, 39.56, 33.24, 28.62, 27.29, 26.06, 24.36, 22.42, 10.51. ESI-MS m/z: 517.9 [M+2], 516.8 [M+1], 258.0 [(M+2)/2].

10C. Off-white solid. $^1$H-NMR (500 MHz, $CD_3OD$): δ 8.24 (b, 2H), 5.56 (s, 2H), 3.14 (m, 4H), 2.91 (t, 4H), 2.46 (m, 4H), 1.63 (m, 8H), 1.50 (m, 4H), 1.34 (b, 20H), 0.89 (t, 6H). $^{13}$C-NMR (500 MHz, $CD_3OD$): δ 172.68, 167.54, 72.54, 41.06, 39.60, 33.29, 29.09, 29.08, 28.94, 28.88, 27.39, 26.24, 24.49, 22.40, 10.50. ESI-MS m/z: 572.5 [M+2], 571.5 [M+1], 286.5 [(M+2)/2].

12C. Off-white solid. $^1$H-NMR (400 MHz, $CD_3OD$): δ 8.23 (b, 2H), 5.56 (s, 2H), 3.14 (m, 4H), 2.91 (t, 4H), 2.45 (m, 4H), 1.63 (m, 8H), 1.50 (m, 4H), 1.32 (b, 28H), 0.89 (t, 6H). $^{13}$C-NMR (500 MHz, $CD_3OD$): δ 172.68, 167.55, 72.54, 41.07, 39.61, 33.33, 29.37, 29.34, 29.29, 29.22, 29.03, 28.94, 27.41, 26.27, 24.54, 22.41, 10.50. ESI-MS m/z: 628.4 [M+2], 627.4 (M+1), 314.3 [(M+2)/2].

Example 2

Biscationic Tartaric Acid-Based Amphiphiles: Charge Location Impacts Antimicrobial Activity As described herein, two series of cationic amphiphiles, termed bola-like and gemini-like amphiphiles, were synthesized with analogous hydrophobic-to-charge ratios but differing charge location and their resulting antibacterial activity assessed. Bola-like amphiphiles exhibited preferential activity against two gram-positive bacteria, with activity increasing with increasing hydrophobicity, whereas gemini-like amphiphiles were active against both gram-positive and gram-negative bacteria, with activity decreasing with increasing hydrophobicity. After identifying compounds from each amphiphile series (bola- and gemini-like), biophysical experiments indicated that both amphiphiles were membrane-active; notably, the gemini-like amphiphile (G7) exhibited a strong dependence on electrostatic interactions for membrane interaction. In contrast, the bola-like amphiphile (B11) exhibited a reliance on both hydrophobic and electrostatic contributions. These results demonstrate that charge location impacts cationic amphiphiles' antibacterial and membrane activity.

1. Introduction

In an effort to overcome current drawbacks of antimicrobial peptides (AMPs), many researchers have synthesized peptidomimetic compounds containing AMPs' key physicochemical properties, namely a net cationic charge and amphiphilic structure. LaDow et al. developed a series of aryl-based bicephalic amphiphiles (two cationic heads, one hydrophobic tail, FIG. 5A) of varying hydrocarbon tail length and determined that bicephalic compounds were more likely to be effective against both gram-positive and gram-negative bacteria than conventional monocationic amphiphiles (LaDow, et al., *European Journal of Medicinal Chemistry* 2011, 46, 4219). Building upon this work, Grenier et al. designed a series of bipyridinium-based gemini amphiphiles (two cationic heads, two hydrophobic tails, FIG. 5A) that demonstrated improved antimicrobial activity over bicephalic amphiphiles, with optimum activity occurring at intermediate hydrocarbon tail lengths (Grenier, et al., *Bioorganic & Medicinal Chemistry Letters* 2012, 22, 4055). Further, Mondal et al. conjugated cationic lysine residues onto glucose to generate bicephalic amphiphiles that may mimic peptide post-translational modifications of AMPs (Mondal, et al., *Carbohydrate Research* 2011, 346, 588). In addition to investigating small molecule amphiphiles as antimicrobial agents, researchers have also studied oligomers (Liu, et al., *Angewandte Chemie-International Edition* 2004, 43, 1158) and polymers (Scorciapino, et al., *Biophys. J.* 2012, 102, 1039; Paslay, et al., *Biomacromolecules* 2012, 13, 2472; Gabriel, et al., *Biomacromolecules* 2008, 9, 2980; Palermo, E. F.; Vemparala, S.; Kuroda, K. *Biomacromolecules* 2012, 13, 1632) in an attempt to develop potent bioactives. Paslay et al., for instance, developed a series of poly(methacrylamide) (co)polymers which demonstrated increasing antimicrobial activity with increasing primary amine content (*Biomacromolecules* 2012, 13, 2472).

In evaluating the diverse array of antimicrobial peptides and amphiphiles that have been developed, one trend becomes apparent: antimicrobial activity is largely influenced by a molecule's hydrophobic-to-charge ratio (Laverty, et al., *International Journal of Molecular Sciences* 2011, 12, 6566; Grenier, et al., *Bioorganic & Medicinal Chemistry Letters* 2012, 22, 4055; LaDow, et al., *European Journal of Medicinal Chemistry* 2011, 46, 4219; Gabriel, et al., *Biomacromolecules* 2008, 9, 2980; Palermo, et al., *Biomacromolecules* 2012, 13, 1632). Very few studies, however, have compared amphiphiles possessing identical hydrophobic-to-charge ratios with varying charge locations. Studies by LaDow et al. revealed that the spacing between cationic charges on structurally similar bicephalic amphiphiles, containing the same hydrophobic-to-charge ratio, does influence antimicrobial activity (LaDow, et al., *European Journal of Medicinal Chemistry* 2011, 46, 4219). As described herein, the specific impact of charge location on cationic amphiphiles' antimicrobial activity was explored, while also delving into amphiphiles' specific membrane activity.

Figure 5:
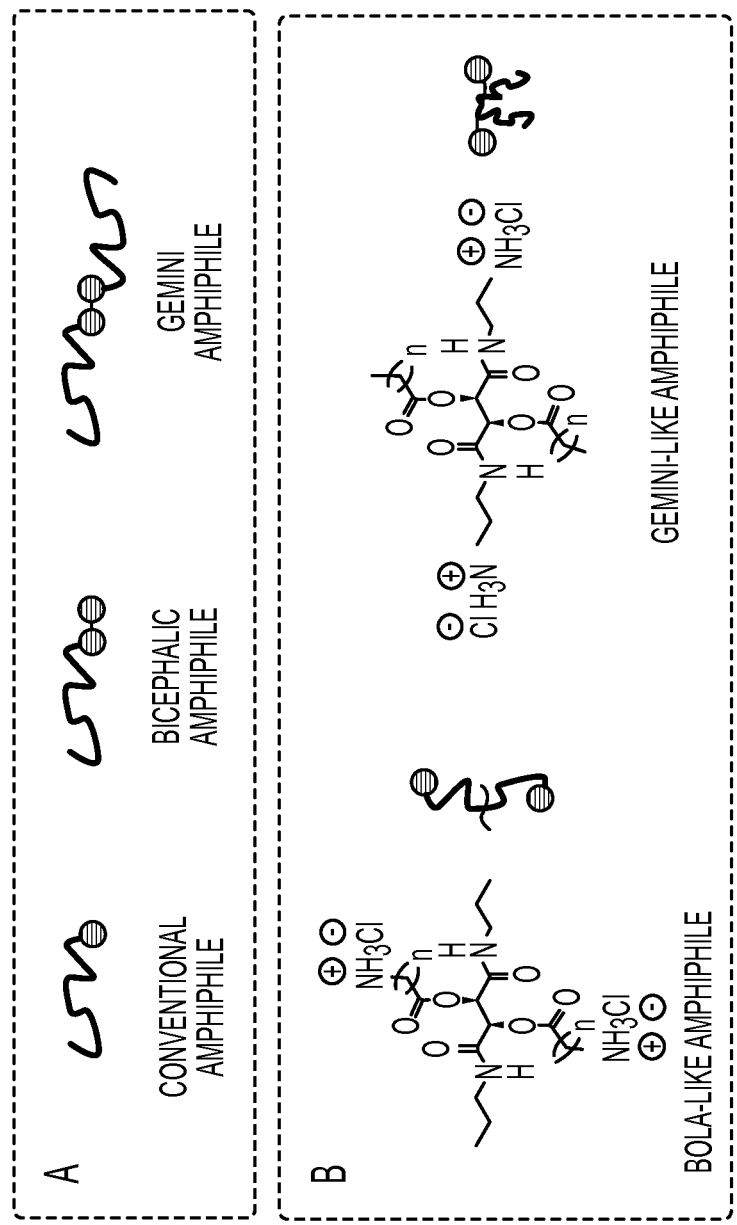
FIG. 5. Representations of amphiphile classes previously investigated for antimicrobial applications (A); Chemical structures and representations of bola-like (left) and gemini-like (right) amphiphiles investigated herein (B).

To investigate this correlation, two series of sugar-based biscationic amphiphiles were synthesized with varying charge locations and varying, yet equivalent, hydrophobic-to-charge ratios. Each series had differing amphiphile architectures as a result of their charge location. Whereas one series more closely resembled gemini amphiphiles (two heads, two tails), which have been widely investigated for antimicrobial applications (Grenier, et al., *Bioorganic & Medicinal Chemistry Letters* 2012, 22, 4055; Zhang, et al., *J. Polymer Chemistry* 2012, 3, 907; Isabel Martin, et al., *Colloids and Surfaces B-Biointerfaces* 2014, 114, 247) the other was more bolaamphiphilic (two heads connected via one tail) in nature (FIG. 5B). It was predicted that the gemini-like amphiphiles would exhibit improved antimicrobial activity compared to the bola-like amphiphiles due to their more facially amphiphilic structure and that each series' antimicrobial activity would increase with increasing hydrophobic-to-charge ratio due to enhanced hydrophobic interactions, leading to membrane permeabilization. Upon successful synthesis of all amphiphiles, their antimicrobial activity was assessed against gram-negative and gram-positive bacteria. Certain compounds were further evaluated based on these results. Specifically, their interactions with model membranes via Langmuir monolayer techniques and isothermal titration calorimetry (ITC) were measured.

2. Materials and Methods

2.1 Materials

All reagents and solvents were purchased from Sigma-Aldrich (Milwaukee, Wis.) and used as received unless otherwise noted. 1 N hydrochloric acid (HCl), concentrated ammonium hydroxide, deuterated methanol ($CD_3OD$), Petri dishes, and cotton swabs were purchased from Fisher Scientific (Fair Lawn, N.J.). Muller-Hinton agar and blank paper disks were purchased from Becton Dickinson (Franklin Lakes, N.J.). 1,2-dioleoyl-sn-glycero-3-phosphocholine (DOPC) and 1,2-dioleoyl-sn-glycero-3-phospho-(1'-rac-glycerol) (DOPG) were purchased from Avanti Polar Lipids, Inc. (Alabaster, Ala.) and used without further purification. N,N-dipropyl tartramide (PT) was prepared according to published procedures (Tounsi, et al., *Journal of Inorganic Biochemistry* 2005, 99, 2423). For broth microdilution assays, bacterial strains *Escherichia coli* ATCC®43895™, *Pseudomonas aeruginosa* ATCC® 14213™, *Listeria monocytogenes* ATCC®49594™, and *Staphylococcus aureus* Rosenbach ATCC® 29213™ were received from the American Tissue Culture Collection (ATCC, Manassass, Va., USA). The *E. coli* and *S. aureus* strains were chosen because they are representative of gram-negative and gram-positive pathogens, respectively.

2.2 Characterization

Proton ($^1H$) and carbon ($^{13}C$) nuclear magnetic resonance (NMR) spectra were obtained using a Varian 400 or 500 MHz spectrometer. Samples were dissolved in deuterated chloroform ($CDCl_3$), dimethyl sulfoxide (DMSO-$d_6$), or $CD_3OD$ using trimethylsilane or deuterated solvent (DMSO-$d_6$ or $CD_3OD$) as an internal reference. Fourier transform infrared (FT-IR) spectra were obtained using a Thermo Scientific Nicolet iS10 spectrophotometer equipped with OMNIC software. FT-IR samples were either pressed into potassium bromide (KBr) discs (1 wt % sample) or solvent-cast onto sodium chloride plates; each spectrum was an average of 32 scans. Molecular weights were determined using a ThermoQuest Finnigan LCQ-DUO system equipped with an atmospheric pressure ionization (API) source, a mass spectrometer (MS) detector, and the Xcalibur data system. Samples were prepared at a concentration of 10 µg/mL in methanol (MeOH) or 50:50 MeOH:dichloromethane (DCM).

2.3 Synthesis of Bola-Like Amphiphiles

2.3.1 Synthesis of tert-butyloxycarbonyl-(Boc-) Protected Alkanoic Acids (3) as Shown in Scheme 6 Below Following modified literature procedures (Orwig, et al., *J Med. Chem.* 2009, 52, 1803; Amara, et al., *Journal of the American Chemical Society* 2009, 131, 10610), bromo-terminated alkanoic acid (1, 3.62 mmol) was either dissolved (1a) or suspended (1b-c) in concentrated ammonium hydroxide (10-100 mL) and stirred for 24-48 h. Upon complete consumption of starting material (monitored by thin layer chromatography, 75:25 hexanes/ethyl acetate with acetic acid), the reaction mixture was concentrated in vacuo to isolate an amine-terminated alkanoic acid intermediate (2). The intermediate was then suspended in a 1:1 mixture of dioxane and 10% sodium carbonate (14 mL each) and gently warmed to 30° C. If necessary, additional water (5 mL) was added to improve stirring. Di-tert-butyl dicarbonate (3.98 mmol) was added and the reaction stirred under reflux temperatures (65° C.) overnight. The reaction mixture was concentrated in vacuo and the resulting crude mixture reconstituted in 1 N HCl and diethyl ether and subsequently extracted with diethyl ether (4×80 mL). The combined organic layers were washed with 1:1 brine/water (80 mL total), dried over magnesium sulfate ($MgSO_4$), and the product (3) isolated in vacuo.

8-Bocaminooctanoic Acid (3a).

Yield: 1.67 g, 78% (off-white solid). $^1$H-NMR (500 MHz, $CDCl_3$): δ 4.56 (br, 1H), 3.10 (m, 2H), 2.34 (t, 2H), 1.63 (m, 2H), 1.45 (m, 17H). $^{13}$C-NMR (500 MHz, $CDCl_3$): δ 179.54, 156.29, 79.34, 40.77, 34.25, 30.16, 29.17, 29.10, 28.64, 26.77, 24.83. IR ($cm^{-1}$, thin film from chloroform, $CHCl_3$): 3367 (NH), 1698 (C=O, acid and carbamate). ESI-MS m/z: 258.1 [M−1].

10-Bocaminodecanoic Acid (3b).

Yield: 1.09 g, 97% (off-white solid). $^1$H-NMR (500 MHz, $CDCl_3$): δ 4.59 (br, 1H), 3.07 (m, 2H), 2.30 (t, 2H), 1.60 (m, 2H), 1.41 (m, 21H). $^{13}$C-NMR (500 MHz, $CDCl_3$): δ 179.61, 156.30, 79.31, 40.81, 34.33, 30.18, 29.49, 29.38, 29.32, 29.22, 28.62, 26.93, 24.91. IR ($cm^{-1}$, thin film from $CHCl_3$): 3367 (NH), 1721 (C=O, acid), 1686 (C=O, carbamate). ESI-MS m/z: 286.1 [M−1].

12-Bocaminododecanoic Acid (3c).

Yield: 1.00 g, 97% (off-white solid). $^1$H-NMR (500 MHz, $CDCl_3$): δ 4.61 (br, 1H), 3.10 (m, 2H), 2.33 (t, 2H), 1.63 (m, 2H), 1.44 (m, 25H). $^{13}$C-NMR (500 MHz, $CDCl_3$): δ 179.56, 156.29, 79.31, 40.85, 34.33, 30.21, 29.66, 29.56, 29.46, 29.41, 29.26, 28.64, 28.45, 27.00, 24.94. IR ($cm^{-1}$, thin film from $CHCl_3$): 3368 (NH), 1722 (C=O, acid), 1686 (C=O, carbamate). ESI-MS m/z: 314.2 [M−1].

2.3.2 Synthesis of 2,3-bis(Boc-Protected Alkanoyl) PTs (4) as Shown in Scheme 6 Below PT (1.36 mmol), 3 (2.99 mmol), and catalytic dimethylaminopyridine (DMAP, 0.57 mmol) were dissolved in anhydrous DCM (27 mL) and dimethylformamide (DMF, 13 mL) under nitrogen. Upon complete dissolution, 1-ethyl-3-(3-dimethylaminopropyl)carbodiimide (EDCI, 5.71 mmol) was added and the reaction stirred overnight under nitrogen. The reaction mixture was concentrated in vacuo, reconstituted in DCM, and washed with aqueous solutions of 10% potassium bisulfite ($KHSO_4$, 3×80 mL) and saturated sodium bicarbonate ($NaHCO_3$, 3×80 mL). The organic layer was then washed with brine (80 mL), dried over $MgSO_4$, and the product (4) isolated in vacuo.

8-Bocaminooctanoyl PT (4a).

Yield: 1.25 g, 95% (pale-yellow solid). $^1$H-NMR (500 MHz, $CDCl_3$): δ 6.27 (br, 2H), 5.60 (s, 2H), 4.57 (br, 2H), 3.20 (m, 4H), 3.10 (m, 4H), 2.40 (t, 4H), 1.63 (m, 4H), 1.44 (m, 38H), 0.91 (t, 6H). $^{13}$C-NMR (500 MHz, $CDCl_3$): δ 172.30, 166.38, 156.20, 79.22, 72.45, 41.44, 40.72, 34.00, 30.18, 29.09, 29.03, 28.65, 26.76, 24.82, 22.86, 11.49. IR ($cm^{-1}$, thin film from $CHCl_3$): 3290 (NH), 1752 (C=O, ester), 1694 (C=O, carbamate), 1655 (C=O, amide). ESI-MS m/z: 737.1 [M+23].

10-Bocaminodecanoyl PT (4b).

Yield: 0.81 g, 95% (pale-yellow solid). $^1$H-NMR (500 MHz, $CDCl_3$): δ 6.24 (br, 2H), 5.61 (s, 2H), 4.54 (br, 2H), 3.21 (m, 4H), 3.10 (m, 4H), 2.40 (t, 4H), 1.62 (m, 4H), 1.51 (m, 46H), 0.91 (t, 6H). $^{13}$C-NMR (500 MHz, $CDCl_3$): δ 171.18, 165.18, 154.96, 78.05, 71.20, 40.17, 39.59, 32.86, 29.04, 28.28, 28.17, 28.12, 27.96, 27.43, 25.73, 23.71, 21.64, 10.25. IR ($cm^{-1}$, thin film from $CHCl_3$): 3280 (NH), 1751 (C=O, ester), 1694 (C=O, carbamate), 1652 (C=O, amide). ESI-MS m/z: 793.2 [M+23].

12-Bocaminododecanoyl PT (4c).

Yield: 0.79 g, quantitative (pale-yellow solid). $^1$H-NMR (400 MHz, $CDCl_3$): δ 6.35 (br, 2H), 5.61 (s, 2H), 4.54 (br, 2H), 3.19 (m, 4H), 3.09 (m, 4H), 2.39 (t, 4H), 1.62 (m, 4H), 1.43 (m, 54H), 0.90 (t, 6H). $^{13}$C-NMR (500 MHz, $CDCl_3$): δ 171.15, 165.20, 154.99, 77.93, 71.27, 40.20, 39.61, 32.86, 29.06, 28.69, 28.49, 28.38, 28.26, 28.22, 28.03, 27.43, 25.79, 23.74, 21.63, 10.27. IR ($cm^{-1}$, thin film from $CHCl_3$): 3281 (NH), 1751 (C=O, ester), 1694 (C=O, carbamate), 1655 (C=O, amide). ESI-MS m/z: 849.3 [M+23].

2.3.3 Synthesis of Bola-Like Amphiphiles (5) as Shown in Scheme 6 Below

Boc groups were deprotected following modified procedures (Han, et al., *Journal of Peptide Research* 2001, 58, 338). In brief, HCl (4M in dioxane, 50.78 mmol) was cooled to 0° C. under nitrogen, 4 added (1.27 mmol), and the reaction stirred at 0° C. for 30 min. The reaction mixture was then warmed to room temperature, stirred an additional 3 h, and concentrated in vacuo. Crude product was dissolved in minimal methanol (10 mL) and aliquots (1 mL) were added to ten 50 mL centrifuge tubes containing diethyl ether (45 mL each), resulting in the precipitation of 5. 5 was isolated via centrifugation (Hettich EBA 12, Beverly, Mass.; 1370×g, 5 min) and decanting the ether. Bola-like amphiphiles will be referred to as Bx, where B denotes bola-like and x refers to the number of methylenes in the acyl arms.

B7 (5a).

Yield: 0.55 g, 96% (off-white solid). $^1$H-NMR (400 MHz, $CD_3OD$): δ 8.25 (br, 2H), 5.57 (s, 2H), 3.15 (m, 4H), 2.92 (t, 4H), 2.48 (m, 4H), 1.64 (m, 8H), 1.51 (m, 4H), 1.39 (br, 12H), 0.90 (t, 6H). $^{13}$C-NMR (500 MHz, $CD_3OD$): δ 172.65, 167.62, 72.58, 41.18, 39.56, 33.24, 28.62, 27.29, 26.06, 24.36, 22.42, 10.51. IR ($cm^{-1}$, KBr): 3422 (NH), 1751 (C=O, ester), 1655 (C=O, amide). ESI-MS m/z: 258.0 [(M+2)/2].

B9 (5b).

Yield: 0.72 g, 95% (off-white solid). $^1$H-NMR (500 MHz, CD$_3$OD): δ 8.24 (br, 2H), 5.56 (s, 2H), 3.14 (m, 4H), 2.91 (t, 4H), 2.46 (m, 4H), 1.63 (m, 8H), 1.50 (m, 4H), 1.34 (br, 20H), 0.89 (t, 6H). $^{13}$C-NMR (500 MHz, CD$_3$OD): δ 172.68, 167.54, 72.54, 41.06, 39.60, 33.29, 29.09, 29.08, 28.94, 28.88, 27.39, 26.24, 24.49, 22.40, 10.50. IR (cm$^{-1}$, KBr): 3288 (NH), 1749 (C=O, ester), 1670 (C=O, amide). ESI-MS m/z: 286.5 [(M+2)/2].

B11 (5c).

Yield: 0.86 g, 97% (off-white solid). $^1$H-NMR (400 MHz, CD$_3$OD): δ 8.23 (br, 2H), 5.56 (s, 2H), 3.14 (m, 4H), 2.91 (t, 4H), 2.45 (m, 4H), 1.63 (m, 8H), 1.50 (m, 4H), 1.32 (br, 28H), 0.89 (t, 6H). $^{13}$C-NMR (500 MHz, CD$_3$OD): δ 172.68, 167.55, 72.54, 41.07, 39.61, 33.33, 29.37, 29.34, 29.29, 29.22, 29.03, 28.94, 27.41, 26.27, 24.54, 22.41, 10.50. IR (cm$^{-1}$, KBr): 3288 (NH), 1744 (C=O, ester), 1668 (C=O, amide). ESI-MS m/z: 627.4 [M+1].

2.4 Synthesis of Gemini-Like Amphiphiles

2.4.1 Synthesis of 2-Bocaminoethyltartramide (2-Boc-AET) (7) as Shown in Scheme 7 Below 2-Boc-AET was prepared according to modified literature procedures (Tounsi, et al., *Journal of Inorganic Biochemistry* 2005, 99, 2423). In brief, dimethyl tartrate (6, 2.43 mmol) was dissolved in anhydrous tetrahydrofuran (7.5 mL) under nitrogen. N-Boc-ethylenediamine (6.79 mmol) was added and the reaction mixture stirred at 40° C. overnight. The crude reaction mixture was concentrated in vacuo and pure product (7) was triturated in diethyl ether (25 mL) and isolated via vacuum filtration. To improve yields, the filtrate was reconcentrated in vacuo, triturated, and vacuum filtered to isolate additional pure product. Yield: 1.93 g, 91% (white solid). $^1$H-NMR (400 MHz, DMSO-d$_6$): δ 7.79 (br, 2H), 6.81 (br, 2H), 5.43 (d, 2H), 4.20 (d, 2H), 3.12 (m, 4H), 2.99 (m, 4H), 1.36 (s, 18H). $^{13}$C-NMR (500 MHz, DMSO-d$_6$): δ 172.84, 156.35, 78.39, 73.22, 40.43, 39.28, 28.92. IR (cm$^{-1}$, KBr): 3356 (NH), 1687 (C=O, carbamide), 1629 (C=O, amide). ESI-MS m/z: 457.2 [M+23].

2.4.2 Synthesis of 2,3-bis(alkanoyl) Boc-AET (8) as Shown in Scheme 7 Below Following methods similar to those described for the synthesis of 4, alkanoic acid (2.53 mmol), 7 (1.51 mmol), and DMAP (0.48 mmol) were dissolved in anhydrous DCM (50 mL) and anhydrous DMF (25 mL) under nitrogen. EDCI (4.83 mmol) was added, the reaction stirred overnight, and concentrated in vacuo. The crude mixture was reconstituted in DCM, washed with aqueous solutions of 10% KHSO$_4$ (3×80 mL), saturated NaHCO$_3$ (3×80 mL), and brine (80 mL), dried over MgSO$_4$, and concentrated in vacuo. This crude product was triturated in hexanes (160 mL) for 4 h and pure product (8) isolated via vacuum filtration.

Nonanoyl-Boc-AET (8a).

Yield: 0.76 g, 93% (white solid). $^1$H-NMR (500 MHz, CDCl$_3$): δ 7.05 (br, 2H), 5.58 (s, 2H), 5.18 (br, 2H), 3.30 (m, 8H), 2.45 (m, 4H), 1.63 (m, 4H), 1.44 (18H), 1.27 (br, 20H), 0.88 (t, 6H). $^{13}$C-NMR (500 MHz, CDCl$_3$): δ 172.37, 167.04, 157.11, 79.94, 72.45, 41.21, 39.99, 34.06, 32.03, 29.46, 29.36, 29.31, 28.62, 24.90, 22.85, 14.31. IR (cm$^{-1}$, thin film from CHCl$_3$): 3369 (NH), 1748 (C=O, ester), 1690 (C=O, carbamide), 1660 (C=O, amide). ESI-MS m/z: 737.4 [M+23].

Undecanoyl-Boc-AET (8b).

Yield: 0.60 g, 84% (white solid). $^1$H-NMR (500 MHz, CDCl$_3$): δ 7.13 (br, 2H), 5.59 (s, 2H), 5.22 (br, 2H), 3.28 (m, 8H), 2.45 (m, 4H), 1.63 (m, 4H), 1.44 (s, 18H), 1.26 (br, 28H), 0.88 (t, 6H). $^{13}$C-NMR (500 MHz, CDCl$_3$): δ 172.39, 167.08, 157.11, 79.90, 72.45, 41.16, 39.98, 34.04, 32.11, 29.80, 29.72, 29.53, 29.51, 29.32, 28.61, 24.90, 22.89, 14.32. IR (cm$^{-1}$, thin film from CHCl$_3$): 3368 (NH), 1742 (C=O, ester), 1690 (C=O, carbamide), 1660 (C=O, amide). ESI-MS m/z: 793.4 [M+23].

Tridecanoyl-Boc-AET (8c).

Yield: 0.89 g, 94% (white solid). $^1$H-NMR (500 MHz, CDCl$_3$): δ 7.07 (br, 2H), 5.58 (s, 2H), 5.18 (br, 2H), 3.28 (m, 8H), 2.44 (m, 4H), 1.63 (m, 4H), 1.44 (s, 18H), 1.26 (br, 36H), 0.88 (t, 6H). $^{13}$C-NMR (500 MHz, CDCl$_3$): δ 172.36, 167.06, 157.11, 79.93, 72.45, 41.22, 39.97, 34.05, 32.14, 29.89, 29.87, 29.86, 29.73, 29.57, 29.53, 29.33, 28.62, 24.91, 22.91, 14.33. IR (cm$^{-1}$, thin film from CHCl$_3$): 3367 (NH), 1740 (C=O, ester), 1689 (C=O, carbamide), 1659 (C=O, amide). ESI-MS m/z: 849.4 [M+23].

2.4.3 Synthesis of Gemini-Like Amphiphiles (9) as Shown in Scheme 7 Below

Boc groups were deprotected following the methods outlined for the synthesis of 5. Briefly, HCl (4M in dioxane, 24.18 mmol) was cooled to 0° C. under nitrogen, 8 added (0.60 mmol), and the reaction stirred at 0° C. for 30 min. If necessary, additional anhydrous dioxane (3 mL) was added to improve stirring. The reaction mixture was warmed to room temperature, stirred an additional 3 h, and concentrated in vacuo. Crude product was dissolved in minimal methanol (6 mL) and aliquots (1 mL) were added to six 50 mL centrifuge tubes containing diethyl ether (45 mL each), resulting in the precipitation of 9. 9 was isolated via centrifugation (Hettich EBA 12, Beverly, Mass.; 1370×g, 5 min) and decanting the ether. Gemini-like amphiphiles will be referred to as Gx, where G denotes gemini-like and x refers to the number of methylenes in the acyl arms.

G7 (9a).

Yield: 0.39 g, 95% (clear, off-white solid). $^1$H-NMR (500 MHz, CD$_3$OD): δ 8.64 (br, 2H), 5.58 (s, 2H), 3.52 (m, 4H), 3.09 (m, 4H), 2.49 (m, 4H), 1.62 (m, 4H), 1.31 (br, 20H), 0.90 (t, 6H). $^{13}$C-NMR (500 MHz, CD$_3$OD): δ 172.92, 168.94, 72.47, 39.46, 36.90, 33.42, 31.84, 29.25, 29.14, 29.00, 24.61, 22.54, 13.28. IR (cm$^{-1}$, KBr): 3455 (NH), 1744 (C=O, ester), 1644 (C=O, amide). ESI-MS m/z: 515.3 [M+1].

G9 (9b).

Yield: 0.42 g, quantitative (off-white solid). $^1$H-NMR (500 MHz, CD$_3$OD): δ 8.62 (br, 2H), 5.57 (s, 2H), 3.50 (m, 4H), 3.08 (m, 4H), 2.47 (m, 4H), 1.61 (m, 4H), 1.29 (br, 28H), 0.90 (t, 6H). $^{13}$C-NMR (500 MHz, CD$_3$OD): δ 172.91, 168.95, 72.47, 39.46, 36.92, 33.43, 31.90, 29.57, 29.48, 29.30, 29.01, 24.62, 22.56, 13.27. IR (cm$^{-1}$, KBr): 3435 (NH), 1739 (C=O, ester), 1652 (C=O, amide). ESI-MS m/z: 571.3 [M+1].

G11 (9c).

Yield: 0.40 g, 94% (white solid). $^1$H-NMR (500 MHz, CD$_3$OD): δ 8.62 (br, 2H), 5.57 (s, 2H), 3.52 (m, 4H), 3.09 (m, 4H), 2.49 (m, 4H), 1.62 (m, 4H), 1.29 (br, 36H), 0.89 (t, 6H). $^{13}$C-NMR (500 MHz, CD$_3$OD): δ 172.90, 168.95, 72.48, 39.47, 36.92, 33.43, 31.91, 29.64, 29.62, 29.61, 29.49, 29.32, 29.02, 24.63, 22.56, 13.27. IR (cm$^{-1}$, KBr): 3448 (NH), 1744 (C=O, ester), 1641 (C=O, amide). ESI-MS m/z: 314.4 [(M+2)/2].

2.5 Antimicrobial Screening

Amphiphiles' antimicrobial activity against gram-negative (*E. coli*) and gram-positive (*S. aureus*) bacteria was first screened using the disk diffusion method (Murray, et al., *Manual of Clinical Microbiology*; 7th ed.; ASM Press: Washington, D C, 1999). Bacteria inocula were grown overnight in nutrient broth (EMD Chemicals, Gibbstown, N.J.) at 37° C. under shaking conditions to give a bacterial count of approximately $10^8$ CFU/mL. Muller-Hinton agar was poured into sterile Petri dishes to a thickness of 4 mm. The agar plate was then inoculated with the bacteria broth culture using a sterile cotton swab. Separately, amphiphiles were dissolved in 4-(2-hydroxyethyl)-1-piperazineethanesulfonic acid) (HEPES) buffer (10 mM, pH 7.4) at concentrations ranging from 0.8 mM to 100 mM. Sterile paper disks (6 mm diameter) were impregnated with 20 µL of test solution and the disks placed onto the inoculated agar plates. Plates were incubated at 37° C. for 20 h, after which zones of inhibition were measured with a ruler. HEPES buffer served as a negative control.

2.6 Broth Microdilution Assay

The broth microdilution method was modified from previous studies (LaDow, et al., *European Journal of Medicinal Chemistry* 2011, 46, 4219). Briefly, amphiphiles were serially diluted 2-fold in tryptic soy broth (TSB) and 100 µL aliquots of each dilution were transferred to a 96-well microtiter plate in triplicate. *S. aureus, L. monocytogenes, E. coli*, and *P. aeruginosa* were grown on tryptic soy agar (TSA) at 37° C. for 24 h, and sterile double-distilled water was inoculated with isolated colonies from these overnight plates. Inoculum concentration was adjusted to $5 \times 10^6$ CFU/mL with ultraviolet-visible (UV-Vis) spectroscopy at 600 nm. Aliquots (100 µL) were transferred to the 96-well microtiter plate to achieve a final concentration of $5 \times 10^5$ CFU/well. Plates were incubated at 37° C. for 24 h. The lowest amphiphile concentration that yielded no visible growth was recorded as the minimum inhibitory concentration (MIC). Cetyltrimethylammonium bromide (CTAB), a cationic amphiphile, served as a positive control that could mimic the proposed bactericidal mechanism of the newly synthesized tartaric acid-based compounds. Sodium dodecyl sulfate (SDS), an anionic amphiphile, served as an additional control, which was not expected to exhibit potent antimicrobial activity against the tested strains.

2.7 Langmuir Monolayer Studies

The ability of amphiphiles to penetrate lipid monolayers was analyzed using a Langmuir surface balance equipped with a custom-built microtrough from KSV-Nima (Biolin Scientific, Espoo, Finland). Lipid solutions were prepared by dissolving DOPC, DOPG, or DOPC/DOPG (1:1 mole ratio) in HPLC grade $CHCl_3$ (~1.2 mg/mL total lipid). After rinsing with an ethanol/methanol mixture, the trough was filled with HEPES buffer and the surface aspirated to remove surface-active particles. Using a Hamilton syringe (Reno, Nev.), small aliquots of lipid solution were applied to the air/buffer interface to obtain varying initial surface pressures ranging from approximately 17 mN/m to 38 mN/m. After solvent evaporation and monolayer equilibration (at least 500 s), 5 µL of B11 (Scheme 6) or G7 (Scheme 7) dissolved in HEPES buffer (5 mM initial amphiphile) was injected into the aqueous subphase via a side port to avoid puncturing the monolayer and the surface pressure increase monitored over time. Data were collected and processed using KSV Nima and Origin software.

2.8 Isothermal Titration Calorimetry

High sensitivity isothermal titration calorimetry (MicroCal VP-ITC, Malvern Instruments, Westborough, Mass.) was used to assess the energetics of amphiphile interactions with lipid vesicles. Large unilamellar vesicles (LUVs) comprised of DOPC or DOPC:DOPG (1:1 mole ratio) were prepared following a published extrusion method (Zhang, et al., *Journal of Biological Chemistry* 2014, 289, 11584). In brief, dried lipid films (pure DOPC or DOPC:DOPG 1:1 mole ratio) were hydrated with HEPES buffer, subject to 5 freeze-thaw cycles, and extruded through 100 nm polycarbonate filters 10 times using a nitrogen-driven device (Lipex Biomembranes, Vancouver, BC, Canada).

The ITC sample cell (~1.4 mL) was filled with solutions of 25 µM B11 (Scheme 6) or G7 (Scheme 7) dissolved in HEPES buffer, and the reference cell was filled with the same buffer. The syringe (250 µL) was filled with LUV dispersions containing 5 mM total lipid. All solutions were degassed for 10 min prior to each experiment. Upon system equilibration and a 1 µL pre-injection, 5 L aliquots were injected into the sample cell every 11 min for the first 4 injections, after which time aliquots were injected in 8-min intervals. Data were collected and processed using proprietary software from MicroCal. All experiments were performed at least in triplicate. Titrations of LUVs into buffer were conducted as negative controls and subtracted from experimental data.

3. Results and Discussion

3.1 Amphiphile Synthesis

To explore the impact of charge location on antimicrobial activity, two series of cationic amphiphiles (gemini- and bola-like) were synthesized with equivalent hydrophobic-to-charge ratios (FIG. 5B). Both series employed tartaric acid, an inexpensive naturally occurring compound produced in fruits (Wu, et al., *Biomacromolecules* 2008, 9, 2921), as a backbone that could provide two distinct chemical moieties for further modification. By altering the charge location on these tartaric acid-based molecules, two structurally diverse amphiphile series were developed.

Scheme 6. Synthesis of bola-like amphiphiles with alkyl chains of varying lengths

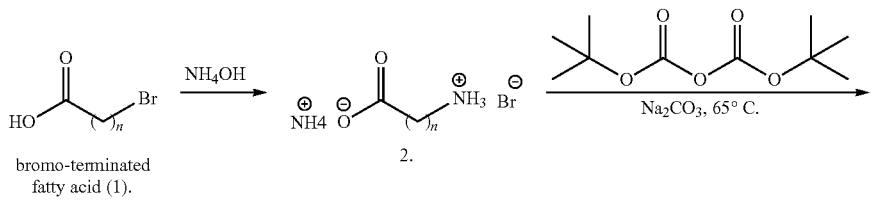

bromo-terminated fatty acid (1).

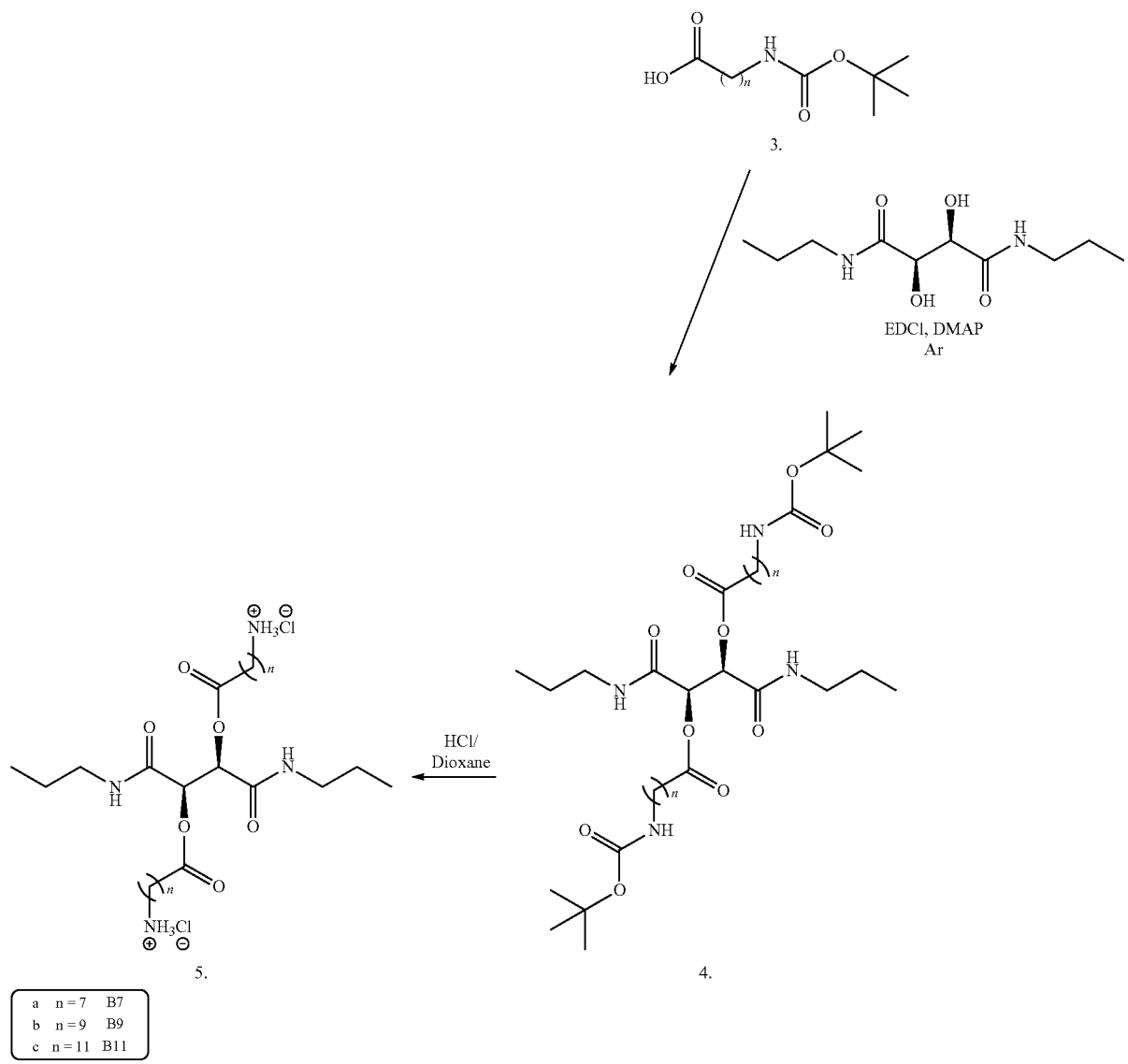

| a | n = 7 | B7 |
| b | n = 9 | B9 |
| c | n = 11 | B11 |

Bola-like amphiphiles resulted when cationic charges were incorporated at the terminal ends of hydrophobic acyl arms (Scheme 6). This series was synthesized by first reacting bromo-containing alkanoic acids (1) with concentrated ammonium hydroxide to generate amine-terminated alkanoic acid intermediates (2). The amine-terminated alkanoic acids were then Boc-protected (3) using di-tert-butyl dicarbonate and subsequently conjugated to a PT backbone using carbodiimide coupling to generate 4. Following successful acylation, 4 was deprotected using HCl in dioxane to generate the final bola-like amphiphiles (5) as chloride salts. All amphiphiles' and intermediates' chemical structures were confirmed via NMR and FT-IR spectroscopies and mass spectrometry.

Scheme 7. Synthesis of gemini-like amphiphiles with alkyl chains of varying lengths

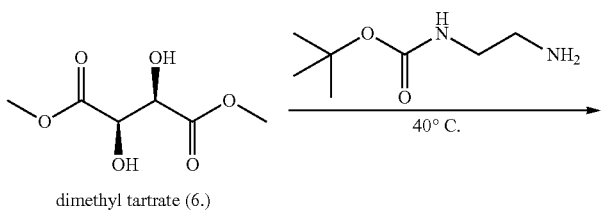

dimethyl tartrate (6.)

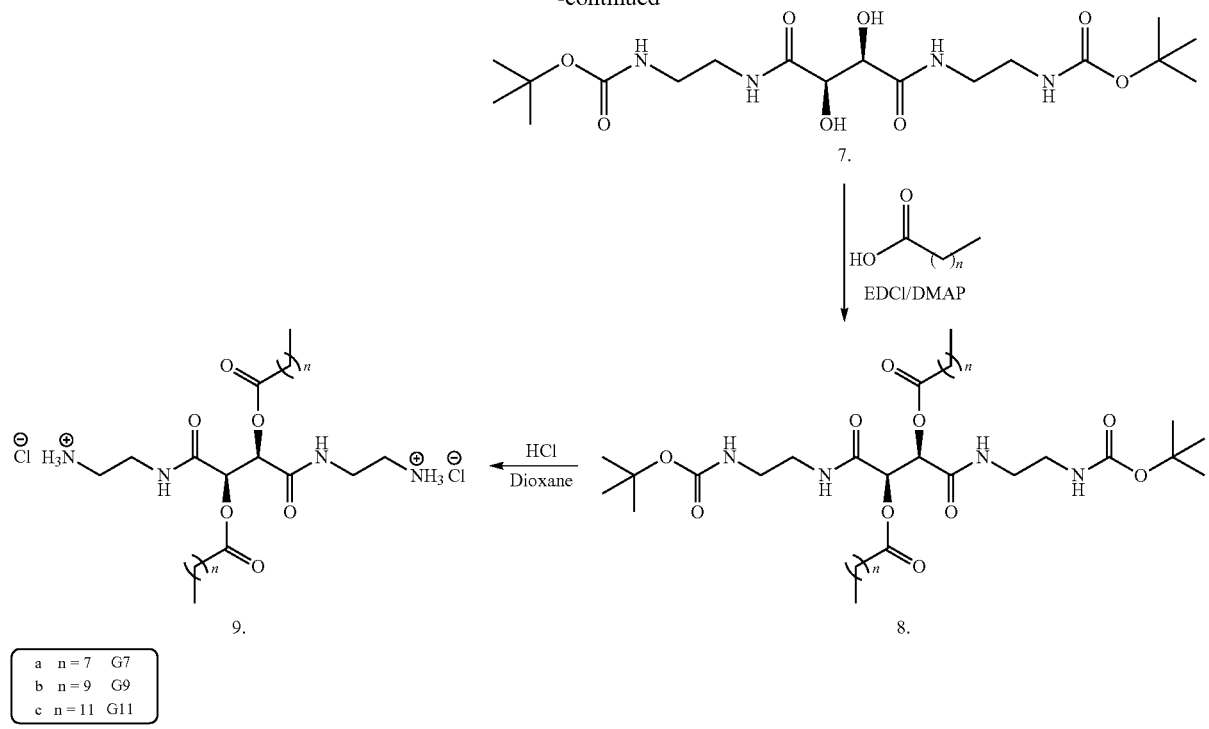

a  n = 7   G7
b  n = 9   G9
c  n = 11  G11

A series of gemini-like amphiphiles was synthesized by incorporating cationic charges at the tartaric acid backbone. These amphiphiles possessed analogous molecular weights, chemical moieties (e.g., number of amine moieties or methylene units), and hydrophobic-to-charge ratios as the bola-like amphiphiles, differing only in their charge location (FIG. 5B). To synthesize these molecules, dimethyl tartrate was first reacted with N-Boc-ethylenediamine via an aminolysis reaction to generate 7 (Scheme 7). 7 was then acylated with alkanoic acids of varying hydrophobic chain lengths using carbodiimide coupling and the Boc protecting groups removed using HCl in dioxane to generate the final amphiphile structures (9). Successful synthesis of the gemini-like amphiphiles and their intermediates was confirmed as described above.

3.2 Antimicrobial Activity

Figure 9:
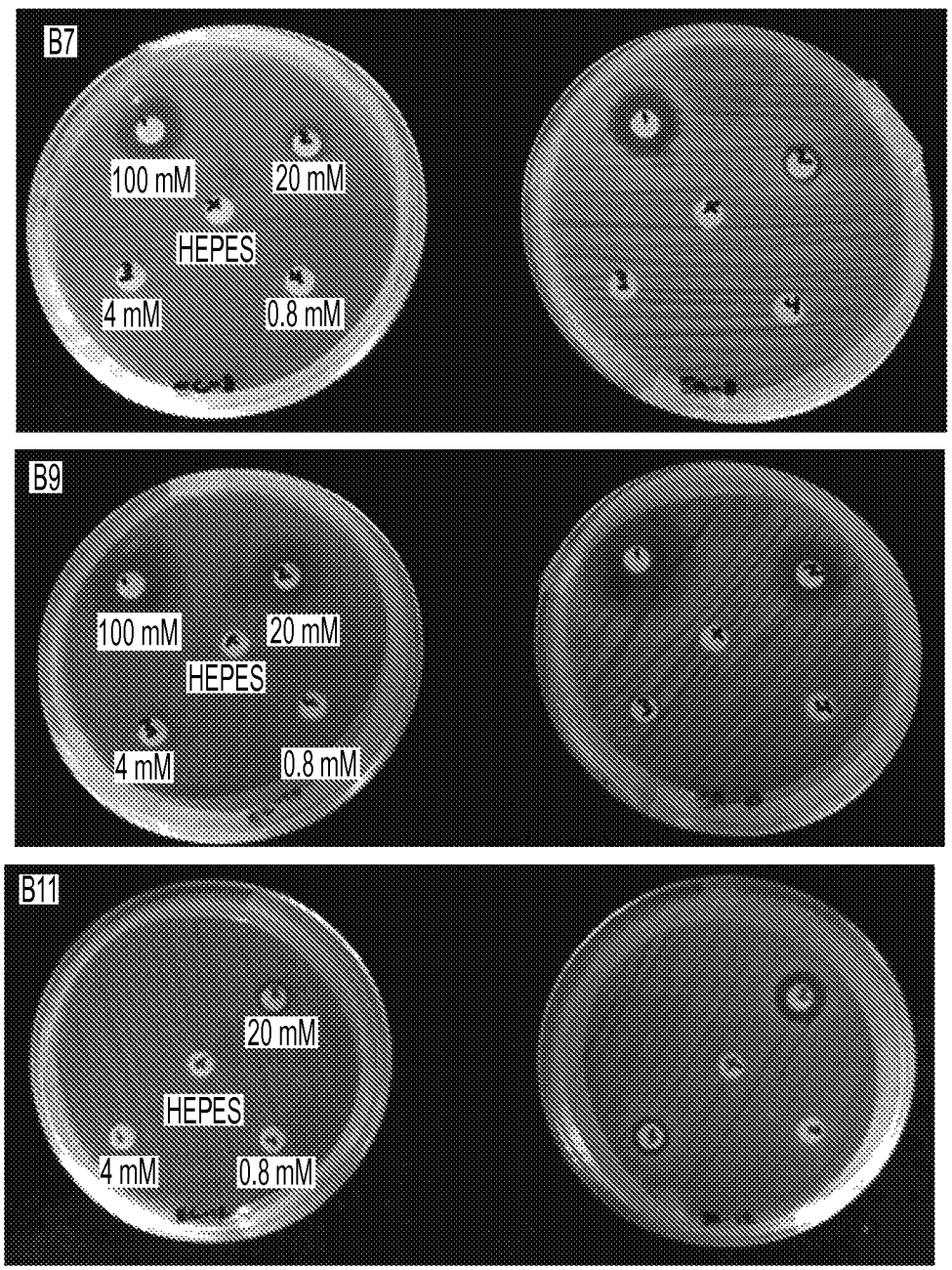
FIG. 9. Antimicrobial screening of bola-like amphiphiles B7 (top), B9 (middle), and B11 (bottom) against E. coli (left) and S. aureus (right) as determined by a disk diffusion assay. Zones of inhibition (i.e., no bacterial growth) correspond to antimicrobial activity.
Figure 10:
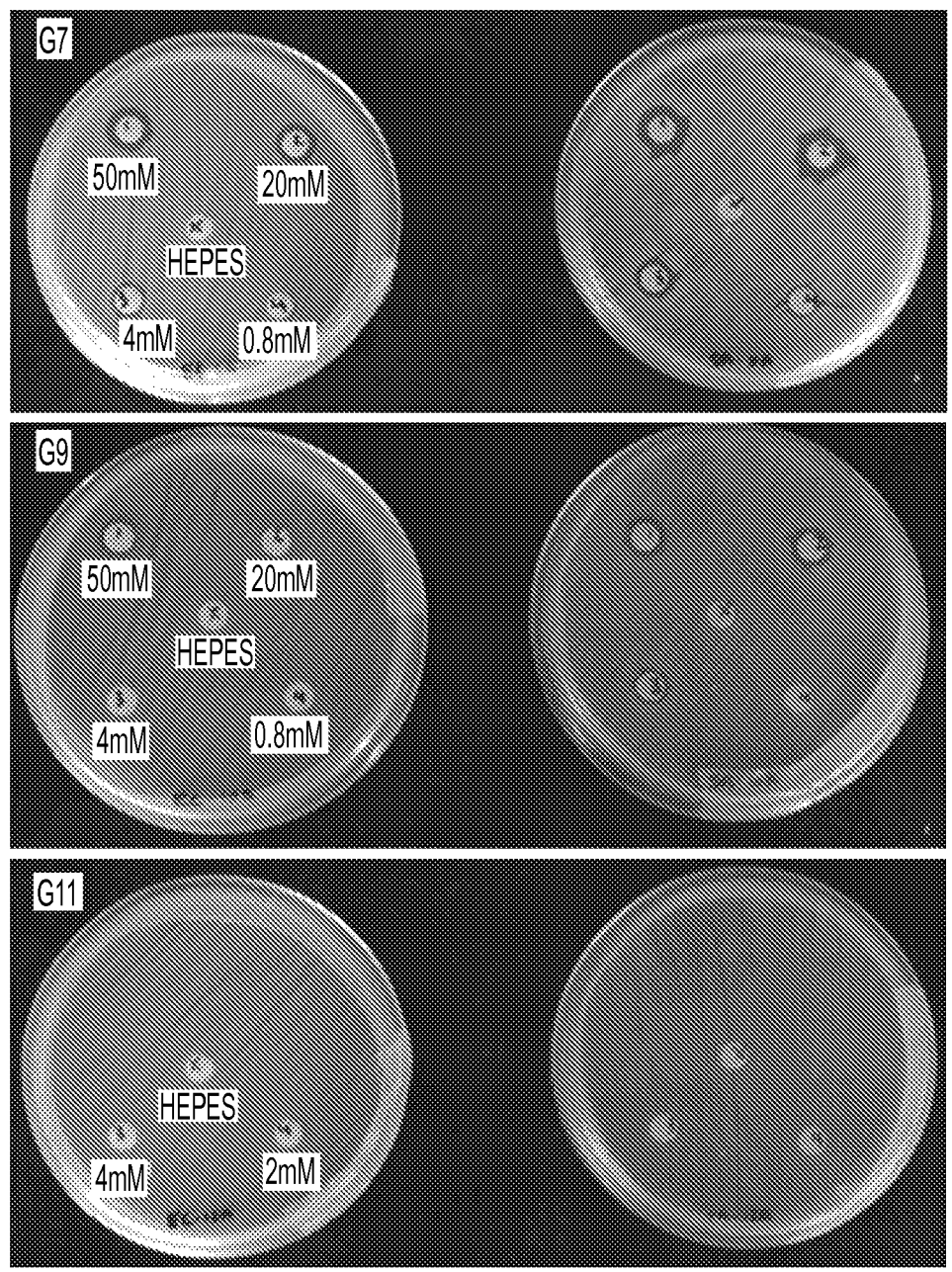
FIG. 10. Antimicrobial screening of gemini-like amphiphiles G7 (top), G9 (middle), and G11 (bottom) against E. coli (left) and S. aureus (right) as determined by a disk diffusion assay. Zones of inhibition (i.e., no bacterial growth) correspond to antimicrobial activity.

Antimicrobial activity was first screened using the disk diffusion method, a qualitative assay which indicated that all amphiphiles except G11—the most hydrophobic gemini-like amphiphile—exhibited activity against *S. aureus, L. monocytogenes, E. coli*, or *P. aeruginosa* in the millimolar range (4-100 mM, FIGS. 9 & 10). While this method is excellent for screening, it is not always suitable for the assessment of hydrophobic compounds as they diffuse more slowly through the agar and may not accurately depict bioactivity (Klancnik, et al., *J. Microbiol. Methods* 2010, 81, 121). Consequently, a broth microdilution assay was carried out to quantitatively assess amphiphile activity. Amphiphiles were incubated with *S. aureus* or *E. coli* in TSB; the lowest amphiphile concentrations that yielded no visible bacterial growth were taken as the MIC values. With the exception of G11, whose antibacterial assessment was hampered by poor aqueous solubility, all amphiphiles exhibited MICs within the low micromolar to low millimolar range (Table 3).

TABLE 3

MICs (μM) of Amphiphiles

| Amphiphile | S. aureus (G+) | L. monocytogenes (G+) | E. coli (G−) | P. aeruginosa (G−) |
|---|---|---|---|---|
| B7 | 500 | 500 | 1000 | 1000 |
| B9 | 125 | 125 | 500 | 250 |
| B11 | 25* | 12.5* | 100 | 50* |
| G7 | 62.5* | 62.5* | 62.5* | 125 |
| G9 | 500 | 250 | 125 | 250 |
| G11 | >200 | >200 | >200 | >200 |
| CTAB | 4 | 8 | 32 | 16 |
| SDS | 1000 | 2000 | >2000 | >2000 |

*Cationic amphiphile treatments possessing MIC values lower than 50 μg/mL

In comparing amphiphiles' antibacterial activity, it became apparent that the hydrophobic-to-charge ratio, which was investigated by varying the number of methylene units present in amphiphiles' hydrophobic domains, significantly influenced amphiphile bioactivity (Table 3). Within the bola-like series (B7, B9, B11), amphiphiles exhibited increasing antibacterial activity as the number of methylene units increased, with B11 demonstrating the highest potency against gram-positive (MIC: 25 and 12.5 μM against *S. aureus* and *L. monocytogenes*, respectively) and gram-negative (MIC: 100 and 50 μM against *E. coli* and *P. aeruginosa*, respectively) bacteria. These results align with previous findings, which indicate increasing acyl chain lengths can result in enhanced bioactivity so long as solubility is not drastically diminished (LaDow, et al., *European Journal of Medicinal Chemistry* 2011, 46, 4219). Furthermore, a recent study by Palermo et al. indicated that antimicrobial activity increases as the spacer length between ammonium ions and a methacrylate polymer backbone increases (Palermo, et al., *Biomacromolecules* 2012, 13, 1632). Given that the methylenes of the bola-like amphiphiles' acyl arms are analogous to such spacer units, these compounds may behave similarly, with longer acyl arms allowing for enhanced membrane penetration and increased bioactivity. In contrast to the trends noted for the bola-like amphiphiles, gemini-like amphiphiles (G7, G9, G11) exhibited decreased antimicrobial activity with increasing acyl chain length. Previous studies have indicated that amphiphiles' with poor solubility exhibit decreased antibacterial activity, as they are incapable of reaching the bacterial membrane (Tew, et al., *Accounts of chemical research* 2010, 43, 30; Grenier, et al., *Bioorganic & Medicinal Chemistry Letters* 2012, 22, 4055; LaDow, et al., *European Journal of Medicinal Chemistry* 2011, 46, 4219). Upon increasing gemini-like amphiphiles' acyl chain length to G11, the amphiphile could not dissolve above 200 µM in TSB. It is plausible that gemini-like amphiphiles' decreased solubility in TSB compromised their antibacterial activity. Although solubility effects may have influenced the gemini-like amphiphile series, G7 exhibited high efficacy against *S. aureus, L. monocytogenes*, and *E. coli* (MICs: 63 µM). As compounds that exhibit MIC values ≤50 µg/mL are commonly considered antimicrobial (Scorciapino, et al., *Biophys. J.* 2012, 102, 1039), broth microdilution studies enabled the identification of two compounds—B11 and G7—whose micromolar MIC values correspond to values ranging from 8.7 and 37.0 µg/mL (denoted by asterisks in Table 3).

When the two series' effects on gram-positive and gram-negative bacteria were compared, varying trends emerged. Bola-like amphiphiles exhibited higher activity against gram-positive organisms *S. aureus* and *L. monocytogenes*, which may result from bola amphiphiles' tendency to penetrate membranes without causing membrane disruption (O'Toole, et al., *Cornea* 2012, 31, 810). Given that gram-negative bacteria contain an additional outer membrane, this potential mechanism of action could have rendered bola-like amphiphiles less active against gram-negative bacteria. Furthermore, as gram-positive and gram-negative bacteria possess different types and ratios of lipids within their cell membranes, it is plausible that the bola-like amphiphiles' enhanced activity against *S. aureus* and *L. monocytogenes* results from interactions with specific lipid components. Gemini-like amphiphiles exhibited no definitive trends against the different bacteria classes; however, G7's high activity against *S. aureus, L. monocytogenes*, and *E. coli* indicates that gemini-like amphiphiles may possess broader activity against both gram-positive and gram-negative bacteria. Given that the bola-like and gemini-like amphiphiles were influenced differently by their hydrophobic-to-charge ratios and exhibited varying activities against gram-positive and gram-negative bacteria, it is plausible that the two series act via different bactericidal mechanisms. Future studies investigating a more expansive series of gram-positive and gram-negative bacteria may further elucidate the potential relationship between bacteria classes and antibacterial activity.

3.3 Biophysical Assessment

Two amphiphiles—B11 and G7—were selected for further experimentation based on their antibacterial activity. As many AMPs interact with bacterial membranes (Park, et al., *International Journal of Molecular Sciences* 2011, 12, 5971; Laverty, et al., *International Journal of Molecular Sciences* 2011, 12, 6566), it was predicted that these two compounds may also interact with bacterial membranes as part of their bactericidal mechanisms. To this end, Langmuir monolayer assays and ITC experiments were conducted to ascertain how the compounds interact with model membrane systems. Given that bola-like and gemini-like amphiphiles exhibited different trends in antibacterial activity, experiments were performed to further understand whether B11 and G7 would exhibit different interactions with model membranes.

3.3.1 Langmuir Monolayer Studies: B11 and G7 can Preferentially Penetrate Anionic Biomembranes Langmuir monolayer techniques were employed to understand amphiphile/lipid interactions. Within these studies, neutral DOPC monolayers served to mimic eukaryotic membranes, whereas anionic DOPG or DOPC:DOPG (1:1 mol ratio) monolayers served to mimic bacterial membranes and elucidate the influence of charge on membrane interactions. Monolayers of varying initial surface pressures were spread at the air/buffer interface and the surface pressure increase monitored upon injection of either B11 or G7 into the aqueous subphase. By plotting the change in surface pressure as a function of initial surface pressure, the x-intercept—corresponding to the amphiphiles' maximum insertion pressure (MIP)—was extrapolated (Calvez, et al., *Biochimie* 2009, 91, 718). MIP values denote the maximum pressure at which insertion into the monolayer is favorable and provide a quantitative means to compare amphiphile/lipid interactions. As MIP values higher than 30-35 mN/m are indicative of biomembrane penetration (Calvez, et al., *Biochimie* 2009, 91, 718), this methodology provides insight into B11 and G7 interactions with eukaryotic and/or bacterial membranes.

Figures 6, 7:
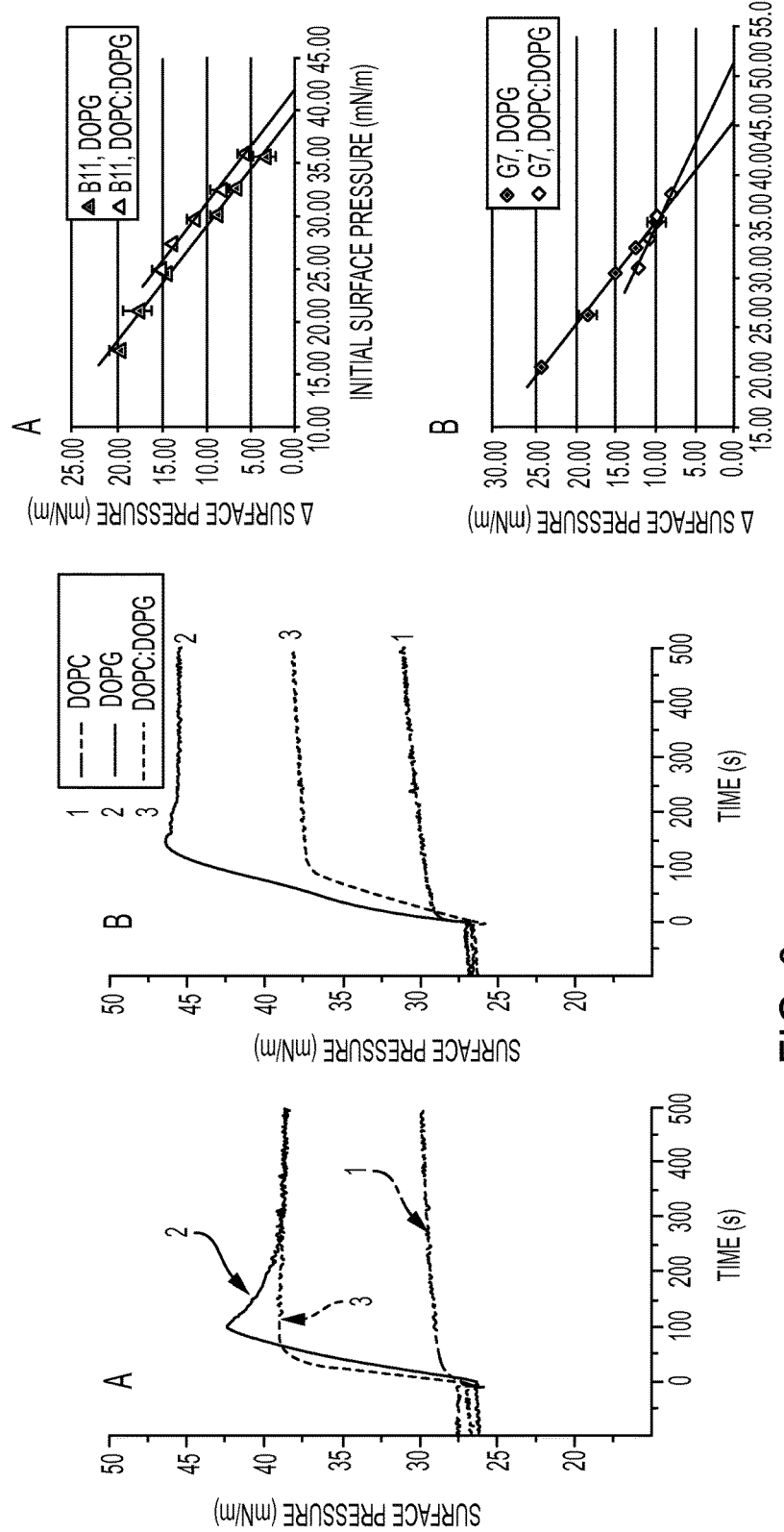
FIG. 6. Raw Langmuir monolayer data depicting the surface pressure increase upon injection of B11 (panel A) or G7 (panel B) into the aqueous subphase of a trough containing DOPC (1), DOPG (2), or DOPC:DOPG (1:1 mol ratio, (3)) monolayers at initial surface pressures of approximately 26 mN/m.
FIG. 7. Interaction of B11 (triangles, A) and G7 (diamonds, B) with DOPG (solid) or DOPC:DOPG (1:1 mol ratio, open) lipid monolayers indicated by change in surface pressure as a function of initial surface pressure.

B11 and G7 exhibited no significant incorporation into neutral DOPC monolayers (FIG. 6), with negligible changes in surface pressure and no linear regression with increasing initial surface pressures. In contrast, both amphiphiles interacted with anionic monolayers (FIG. 6), exhibiting a surface pressure increase, which decreased with higher initial surface pressures (FIG. 7). This enhanced membrane activity in the presence of anionic lipids has been previously reported (Scorciapino, et al., *Biophys. J* 2012, 102, 1039) and may indicate that the amphiphiles behave similarly to cationic AMPs, which initially interact with bacterial membranes via electrostatic interactions (Laverty, et al., *International Journal of Molecular Sciences* 2011, 12, 6566; Brogden, K. A. *Nature Reviews Microbiology* 2005, 3, 238). In DOPG and DOPC:DOPG monolayers, B11 exhibited MIP values of 40 and 42 mN/m, respectively, whereas G7 exhibited MIP values of 46 and 52 mN/m, respectively (FIG. 7). In general, G7's higher MIP values indicate enhanced interactions with anionic monolayers. As all MIP values were greater than the biomembrane lateral pressure and comparable to MIP values of known AMPs (Calvez, et al., *Biochimie* 2009, 91, 718), it is expected that both B11 and G7 are capable of intercalating within anionic bacterial membranes, suggesting that these amphiphiles may behave similarly to AMPs and target the bacterial membrane as part of their bactericidal mechanism. In comparing amphiphile interactions with the two different anionic lipid systems, both amphiphiles exhibited higher MIP values in the presence of DOPC:DOPG monolayer mixtures. This phenomenon could result from DOPC's smaller head group area (Kleinschmidt, et al., *Biophys. J.* 2002, 83, 994) enabling a more favorable insertion of amphiphiles into the lipid monolayer.

3.3.2 Langmuir Monolayer Studies Suggest Electrostatic Contributions in Membrane Interaction Differ for B11 and G7

In addition to extrapolating MIP values, a second parameter that provides useful information for analyzing membrane interaction is the maximum surface pressure increase measured during Langmuir monolayer studies (Calvez, et al., *Biochimie* 2009, 91, 718). Through comparing the amphiphiles' maximum surface pressure increase in the presence of both DOPG and DOPC:DOPG, we could better understand the influence of monolayer charge on amphiphile adsorption. This value is typically obtained by comparing adsorption curves with the same initial surface pressure; however, both amphiphiles exhibited a plateau in maximum surface pressure increase at lower initial surface pressures, likely due to their equilibrium with the bulk aqueous phase. Consequently, the lowest initial surface pressures plotted in FIG. 7, correspond to the maximum surface increase for a given amphiphile/lipid system.

G7 exhibits a maximum surface pressure increase of 24 mN/m in the presence of pure DOPG, which decreases to 12 mN/m in the presence of DOPC:DOPG (FIG. 7B). This dependence of maximum surface pressure increase on the mole fraction of anionic lipid has been previously reported (Kennedy, et al., *Biochemistry* 1997, 36, 13579) and indicates an electrostatic contribution in membrane binding. B11 also exhibits a decrease in maximum surface pressure increase when changing the lipid system from DOPG to DOPC:DOPG, yet to a smaller extent (20 mN/m to 15 mN/m, FIG. 7A) than G7; this result reflects a lesser dependence on electrostatic interactions. These results are further emphasized in FIG. 6; B11 behaves similarly in the presence of both DOPG and DOPC:DOPG, whereas G7 exhibits a drastic decrease in surface pressure increase upon changing the lipid system from DOPG to DOPC:DOPG. The notable difference in electrostatic contribution suggests that B11 relies on a combination of electrostatic and hydrophobic interactions to elicit bacterial death, whereas G7's bactericidal mechanism may be largely driven by electrostatic interactions. B11's reliance on both hydrophobic and electrostatic interactions for monolayer intercalation, could suggest that the bola-like compounds are drawn to the bacterial membrane via an initial electrostatic interaction followed by intercalation into the hydrophobic membrane interior via hydrophobic interactions. G7's strong electrostatic interaction with anionic monolayers suggests that gemini-like compounds may interact predominantly with anionic components of bacterial membranes, including PG headgroups, lipopolysaccharide (LPS, found in gram-negative bacteria), and lipoteichoic acids (LTA, found in gram-positive bacteria). A primarily electrostatic mechanism of action could be hampered by increasing hydrophobic content, potentially resulting in gemini-like amphiphiles' decreased activity with increasing hydrophobic-to-charge ratio.

3.3.3 ITC Studies: B11 and G7 Operate Via Different Bactericidal Mechanisms

Figure 8:
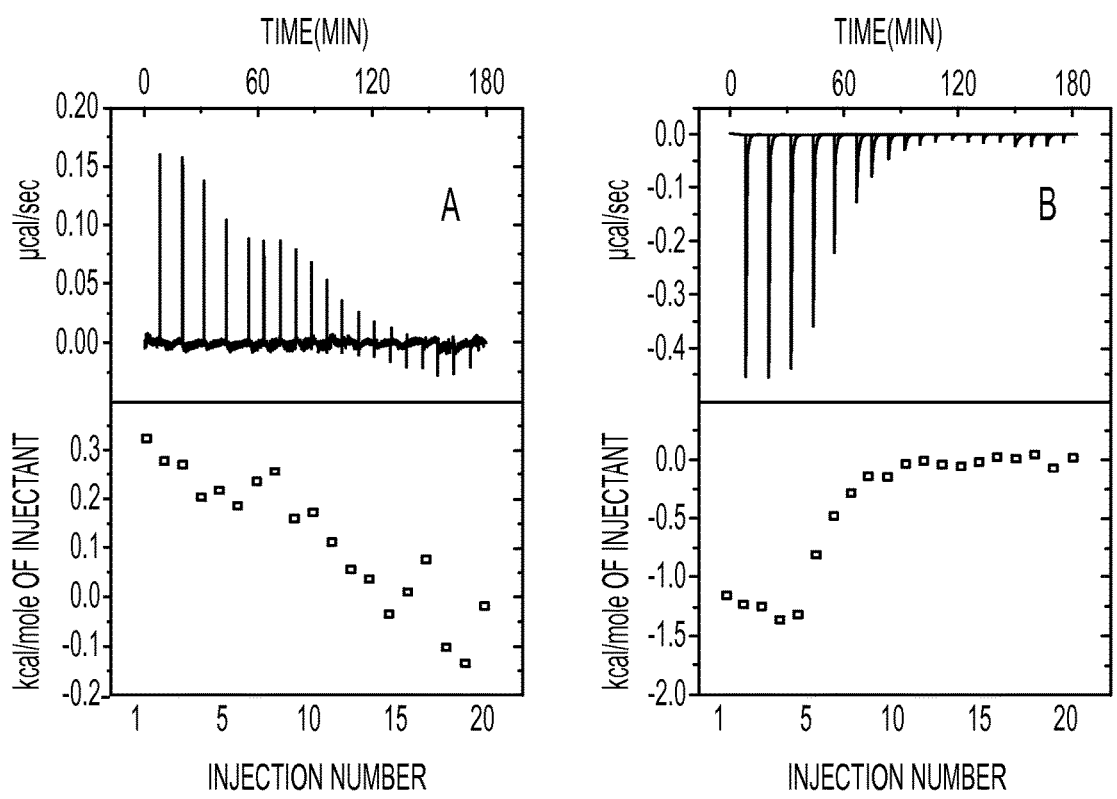
FIG. 8. ITC traces obtained from titrating DOPC:DOPG (1:1 mol ratio) into B11 (A) and G7 (B). Upper curves depict heat flow as a function of time, whereas lower curves depict the corresponding integrated area of each peak as a function of injection number.
Figure 11:
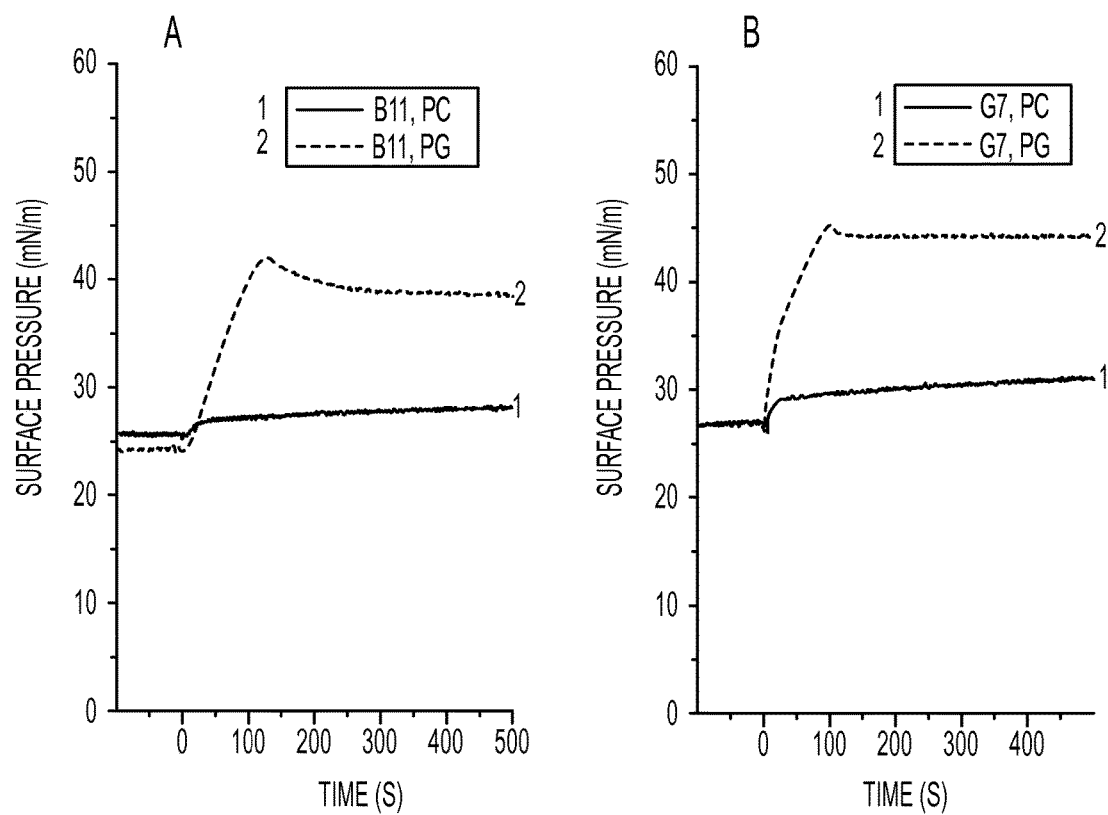
FIG. 11. Langmuir monolayer data depicting surface pressure increase upon injection of B11 (panel A) or G7 (panel B) into the aqueous subphase of a trough containing either DOPC (1) or DOPG (2) lipid monolayers at initial surface pressures of approximately 25 mN/m.
Figure 12:
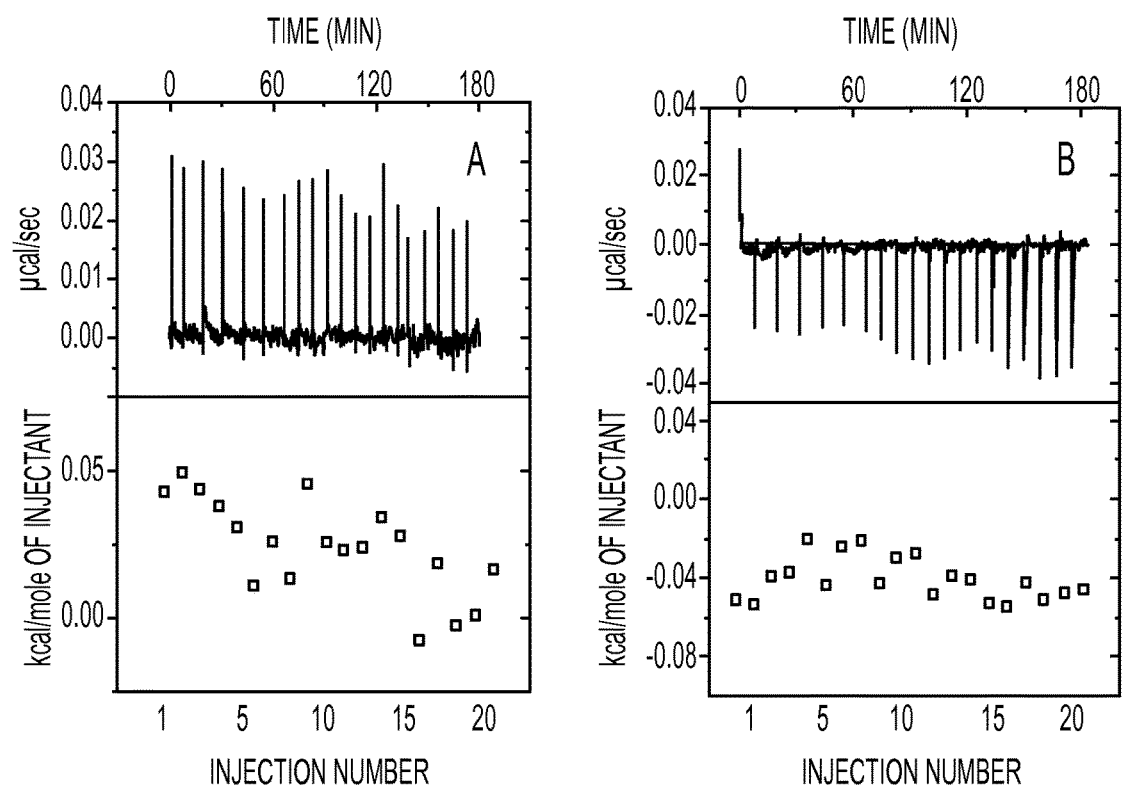
FIG. 12. ITC traces obtained from titrating DOPC into B11 (panel A) and G7 (panel B). Upper curves depict heat flow as a function of time, whereas lower curves depict the corresponding integrated area of each peak as a function of injection number. Heat flow was negligible for both titrations.
Figure 13:
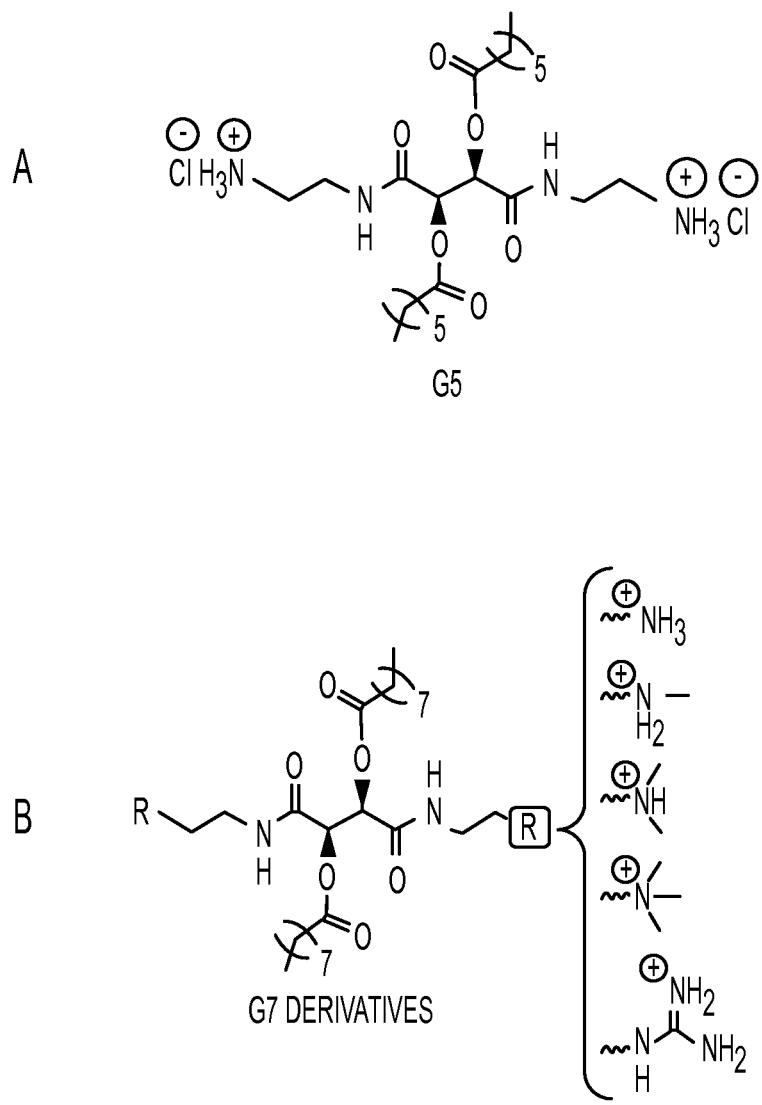
FIG. 13. A. Structure of G5 amphiphile; and B. Structures of G7 derivatives.

While Langmuir monolayer studies provided valuable insight into amphiphile's interactions with biomembranes, ITC was used to investigate amphiphiles' interactions with bilayers, a more relevant model membrane system. LUVs comprised of pure DOPC or DOPC:DOPG (1:1 mol ratio) were prepared to mimic eukaryotic and bacterial membranes, respectively; these LUVs were titrated into a sample cell containing amphiphile solution (i.e., B11 or G7 dissolved in HEPES buffer). Both B11 and G7 exhibited no interactions with neutral DOPC LUVs, evidenced by negligible heat signals during the titration (see, FIGS. 11 and 12). As eukaryotic membranes also exhibit a net neutral charge, these results may indicate that both amphiphiles would interact minimally with eukaryotic cells, a correlation that has been previously depicted by Epand et al. (*J. Mol. Biol.* 2008, 379, 38). In investigating anionic LUVs (i.e., DOPC:DOPG), both amphiphiles exhibited binding interactions, and the heats associated with these binding interactions generally decreased as the titrations progressed. As LUVs were added into the titration cell amphiphiles would bind to LUVs, leaving less amphiphiles available for binding and resulting in smaller heat signals in subsequent LUV injections until all amphiphiles were removed from the bulk solution (Seelig, J. *Biochim. Biophys. Acta-Rev. Biomembr.* 1997, 1331, 103; Breukink, et al., *Biochemistry* 2000, 39, 10247; Domingues, et al., *Langmuir* 2013, 29, 8609; Binder, et al., *Biophys. J.* 2003, 85, 982). B11 exhibited endothermic binding interactions, indicated by a positive enthalpy change (FIG. 8A). Such binding interactions often result from the displacement of counterions or water molecules as a result of the hydrophobic effect (Seelig, J. *Biochim. Biophys. Acta-Rev. Biomembr.* 1997, 1331, 103; Gabriel, et al., *Langmuir* 2008, 24, 12489; Seelig, J. *Biochim. Biophys. Acta-Biomembr.* 2004, 1666, 40), suggesting B11's hydrophobic domain may penetrate into the hydrophobic membrane interior of the anionic LUVs and that binding is largely influenced via hydrophobic interactions. As B11 did not interact with DOPC (i.e., neutral) LUVs yet did interact with DOPC:DOPG (i.e., anionic) LUVs, it was predicted that an initial electrostatic interaction occurred. Although electrostatic binding results in exothermic heat signals, it is plausible B11's stronger dependence on the hydrophobic effect resulted in the observed positive enthalpy change (Livne, et al., *Chemistry & Biology* 2009, 16, 1250).

In contrast to B11, G7 exhibited a negative enthalpy change under identical conditions (FIG. 8B), which suggests an exothermic, electrostatic interaction between G7 and anionic LUVs (Epand, et al., *J Mol. Biol.* 2008, 379, 38). This exothermic interaction supports Langmuir monolayer data, which indicated that G7's membrane insertion activity involved a larger electrostatic contribution than that of B11.

The diverging energetics of binding indicate that B11 and G7 may act via different bactericidal mechanisms. Gemini-like amphiphiles demonstrated activity against both gram-positive and gram-negative organisms. As G7 exhibits electrostatic binding interactions with anionic LUVs, these amphiphiles may interact favorably with the negatively charged lipid components of gram-positive and gram-negative bacteria (e.g., lipid headgroups, LPS, or LTA), enabling specific activity against bacteria. For instance, G7 may interact with LPS on the outer membrane of *E. coli*, potentially neutralizing LPS or displacing divalent cations associated with LPS and ultimately distorting the outer membrane (Park, et al., *International Journal of Molecular Sciences* 2011, 12, 5971; Laverty, et al., *International Journal of Molecular Sciences* 2011, 12, 6566). This electrostatic interaction may have been hampered upon increasing compounds' hydrophobic-to-charge ratio, resulting in decreased activity. After this initial electrostatic interaction, gemini-like compounds likely insert their hydrophobic tails into the hydrophobic membrane interior; however, this interaction was not observed during biophysical studies. In contrast, bola-like amphiphiles exhibited preferential activity against gram-positive bacteria with B11 demonstrating endothermic binding interactions with anionic LUVs, indicative of the entropically driven hydrophobic effect. These molecules likely rely on an initial electrostatic interaction, with the negatively charged peptidoglycan matrix of gram-positive bacteria, followed by intercalation into the membrane's hydrophobic domain, potentially adopting a U-shape or membrane-spanning conformation. This reliance on hydrophobic interactions could explain why bola-like amphiphiles exhibited enhanced activity upon increasing their hydrophobic-to-charge ratio. Modeling studies are currently underway to understand this conformation. Over time, this intercalation may result in membrane destabilization through various potential mechanisms, such as membrane thinning or pore formation (Park, et al., *International Journal of Molecular Sciences* 2011, 12, 5971; Laverty, et al., *International Journal of Molecular Sciences* 2011, 12, 6566; Brogden, K. A. *Nature Reviews Microbiology* 2005, 3, 238; Mondal, et al., *Carbohydrate Research* 2011, 346, 588). In summary, the antimicrobial studies in conjunction with biophysical experiments described herein indicate the significant influence of charge location on amphiphile activity.

4. Conclusions

Bola-like and gemini-like amphiphiles were synthesized to understand the specific influence of charge location on antibacterial activity. Bola-like amphiphiles exhibited increased activity with increasing hydrophobic-to-charge ratios, likely resulting from a combination of both hydrophobic and electrostatic interactions with the bacterial membranes. Gemini-like amphiphiles demonstrated a different trend, with antibacterial activity increasing as hydrophobic-to-charge ratios decreased. This phenomenon may have resulted from the decreased solubility of more hydrophobic gemini-like amphiphiles or from gemini-like amphiphiles relying primarily on electrostatic interactions in their bactericidal mechanism. Additionally, both amphiphiles exhibited differences in bioactivity against the tested gram-positive bacteria and gram-negative bacteria, further suggesting that the two amphiphile series possess different bactericidal mechanisms and may interact with different components of bacteria membranes. These studies reveal that, in addition to the hydrophobic-to-charge ratio, charge location significantly modulates cationic amphiphiles' antibacterial activity and bactericidal mechanism. Through understanding this influence of charge location, antimicrobial agents could be designed to target different bacteria types and/or membrane structures.

Example 3

Antimicrobial Amphiphiles with Enhanced Activity

The antimicrobial activity of the G7, G9 and B11 amphiphiles against a variety of bacterial species was evaluated using MIC studies. Specifically, Standard CLIS/NCCLS broth microdilution assays were utilized for both BSL2 and BSL3 organisms in a 96-well format ((CLSI/NCCLS) CaLSI. Methods for antimicrobial susceptibility testing of aerobic bacteria: Approved standard. Wayne, Pa.: CLIS, 2007; (CLSI/NCCLS) CaLSI. Methods for dilution antimicrobial susceptibility tests for bacteria that grow aerobically; Approved standard. Wayne, Pa.: CLIS, 2009). The compounds were diluted at 32 mg/mL to 0.125 mg/mL in 2-fold dilutions performed in triplicate. The time course of killing was established by evaluating viability after exposure to compound after 18 hours. The MIC is defined as the lowest concentration of compound that confers a no-growth phenotype as noted by the naked eye. These studies demonstrate broad spectrum activity and impact of the amphiphiles (Table 4).

TABLE 4

| MIC Values (ug/mL) | | | |
|---|---|---|---|
| | G7 | G9 | B11 |
| Vero Cell Cytotoxicity | >50 | 50 | 50 |
| A. baumannii | >50 | >50 | >50 |
| B. cereus | 6.25 | 6.25 | 50 |
| B. cepacia | >50 | >50 | >50 |
| B. neotomae | 3.125 | 3.125 | 25 |
| E. faecium | 6.25 | 6.25 | 25 |
| K. pneumoniae | 50 | >50 | >50 |
| L. pneumophilia | 12.5 | 25 | >50 |
| P. aeruginosa | 25 | >50 | >50 |
| S. aureus | 6.25 | 6.25 | 25 |
| Y. pseudotuberculosis | 12.5 | 6.25 | >50 |
| S. epidermidis | 12.5 | 6.25 | 25 |

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:
1. A compound of formula II:

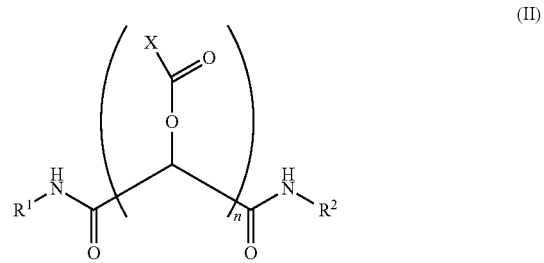

(II)

wherein:
R$^1$ is a (C$_1$-C$_6$)alkyl that is substituted with one or more NR$_a$R$_b$;
R$^2$ is a (C$_1$-C$_6$)alkyl that is substituted with one or more NR$_a$R$_b$;
each X is independently (C$_4$-C$_{12}$)alkyl;
R$_a$ is each independently H or (C$_1$-C$_6$)alkyl;
R$_b$ is each independently H, (C$_1$-C$_6$)alkyl or —C(=NH)NH$_2$; and
n is 1, 2, 3, 4, 5, 6, 7, or 8;
or a salt thereof.

2. The compound or salt of claim 1, wherein R$^1$ is methyl, ethyl, propyl, isopropyl, butyl, isobutyl, or sec-butyl, substituted with one or more NR$_a$R$_b$.

3. The compound or salt of claim 1, wherein R$^2$ is methyl, ethyl, propyl, isopropyl, butyl, isobutyl, or sec-butyl, substituted with one or more NR$_a$R$_b$.

4. The compound or salt of claim 1, wherein each X is independently (C$_8$)alkyl.

5. The compound or salt of claim 1, wherein each X is independently (C$_9$)alkyl.

6. The compound or salt of claim 1, wherein each X is independently (C$_{10}$)alkyl.

7. The compound or salt of claim 1, wherein each X is independently $(C_{11})$alkyl.

8. The compound or salt of claim 1, wherein each X is independently $(C_{12})$alkyl.

9. The compound or salt of claim 1, wherein n is 2.

10. The compound or salt of claim 1, which is a compound of formula (IIc):

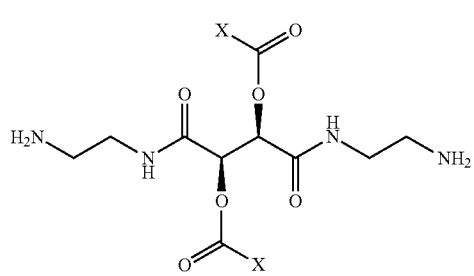

(IIc)

or a salt thereof.

11. The compound or salt of claim 1, which is selected from the group consisting of:

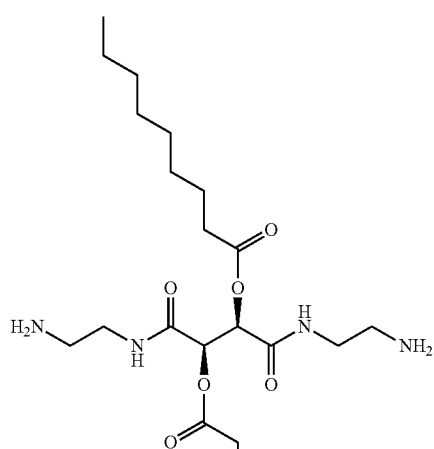

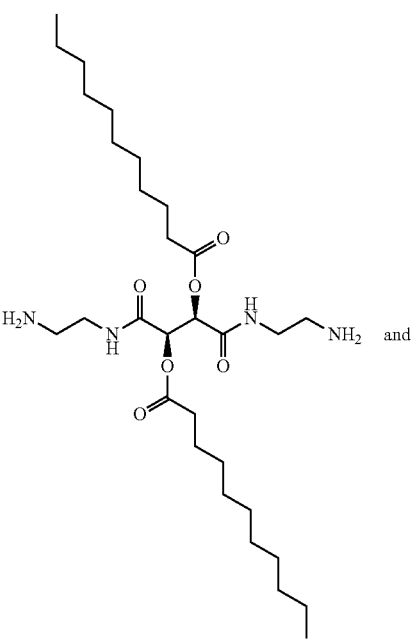

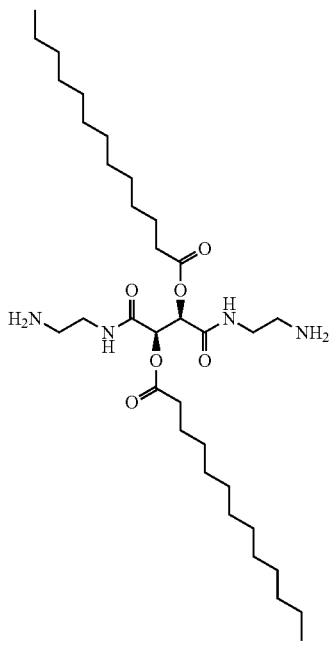 [SMILES: CCCCCCCCCCCCC(=O)O[C@@H](C(=O)NCCN)[C@@H](OC(=O)CCCCCCCCCCCC)C(=O)NCCN]

or a salt thereof.

12. The salt of claim 1, which is selected from the group consisting of:

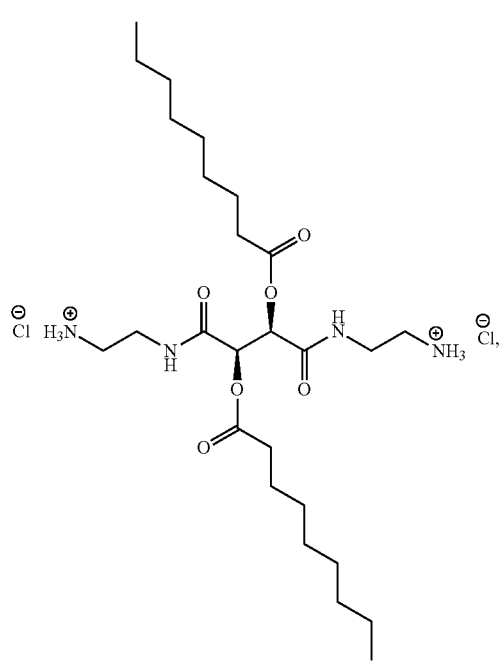
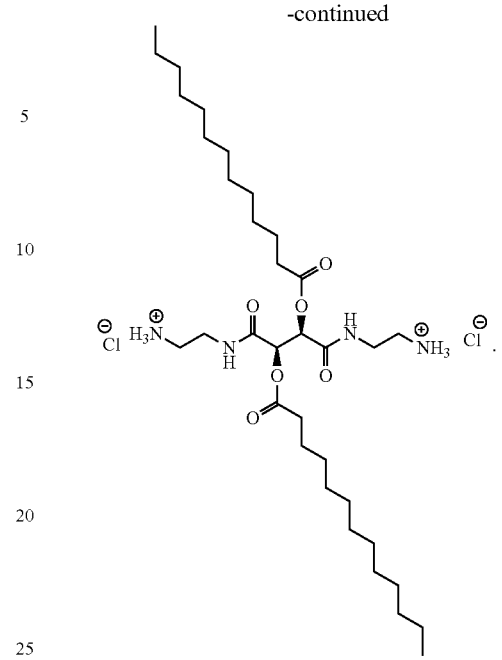
13. A pharmaceutical composition comprising a compound as described in claim 1, or a pharmaceutically acceptable salt thereof, and a pharmaceutically acceptable carrier.
14. The compound or salt of claim 10, wherein each X is independently $(C_7)$alkyl, $(C_9)$alkyl or $(C_{11})$alkyl.
15. The compound or salt of claim 1, which is:
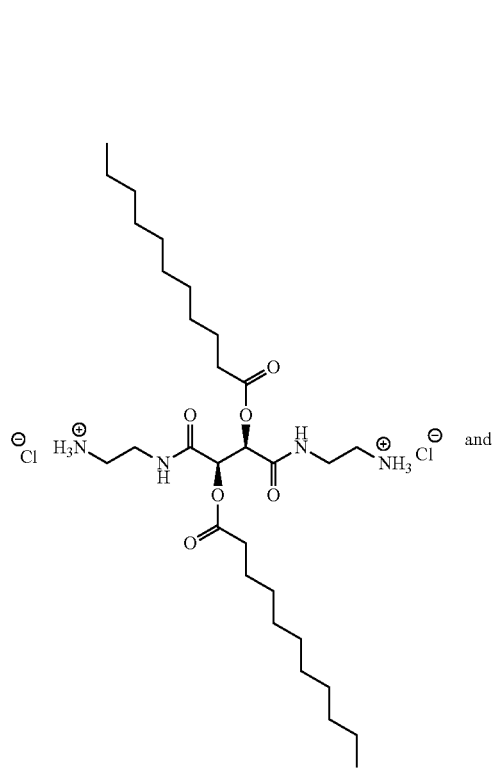 and
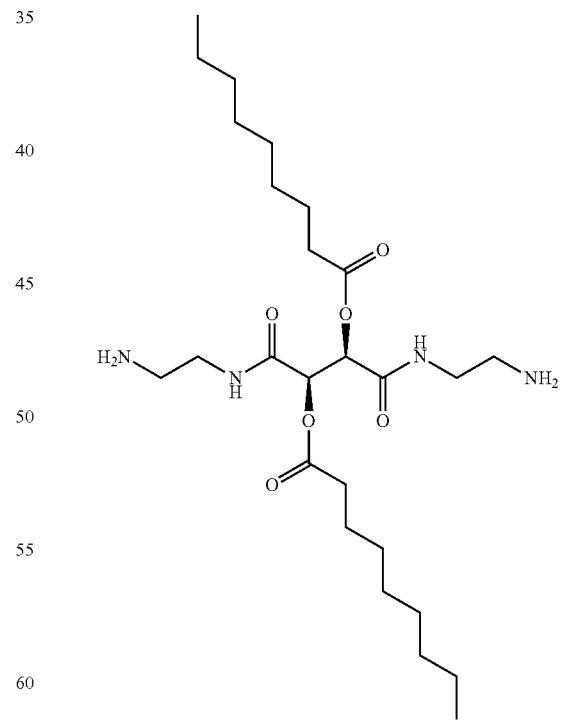
or a salt thereof.
* * * * *